United States Patent [19]

Kim et al.

[11] Patent Number: 5,260,327
[45] Date of Patent: Nov. 9, 1993

[54] METHODS FOR INHIBITING THE PROLIFERATION OF BRAIN AND HEPATIC METASTASES BY USING LONIDAMINE

[75] Inventors: Jae H. Kim, West Bloomfield, Mich.; Sang H. Kim, Flushing, N.Y.; Alan Alfieri, Garden City, N.Y.; Charles W. Young, New York, N.Y.

[73] Assignee: Sloan-Kettering Institute for Cancer Research, New York, N.Y.

[21] Appl. No.: 925,813

[22] Filed: Aug. 4, 1992

Related U.S. Application Data

[63] Continuation of Ser. No. 526,516, May 21, 1990, abandoned, which is a continuation-in-part of Ser. No. 783,209, Oct. 2, 1985, abandoned.

[51] Int. Cl.⁵ .................. A61K 31/415; A61K 31/11
[52] U.S. Cl. .................................. 514/405; 514/700; 424/10
[58] Field of Search .................. 514/200, 405; 424/10

[56] References Cited

PUBLICATIONS

Field, J. B., et al., Cancer Res., 24(1):40–42, 57 (1964).
Kim, J. H., et al., Cancer Res., 46:1120–1123 (1986).
Kim, J. H. et al.: Clinical Study of the Sequence of Combined Hyperthermia and Radiation Therapy of Malignant Melanoma. In Hyperthermic Oncology, vol. 1, J. Overgaard (Ed.), London, Philadelphia; Taylor and Francis, 1984, pp. 387–390.

Primary Examiner—Frederick E. Waddell
Assistant Examiner—T. J. Criares
Attorney, Agent, or Firm—John P. White

[57] ABSTRACT

This invention provides methods for inhibiting the proliferation of brain or hepatic metastases, in vivo, by contacting the cells with lonidamine and radiation.

10 Claims, 16 Drawing Sheets

○ RADIATION ALONE
● RADIATION + LONIDAMINE (50 μg/ml)
▲ RADIATION + HEAT (41.5°C, 60 min)
△ RADIATION + HEAT (41.5°C, 60 min)
   + LONIDAMINE (50 μg/ml)

METHODS FOR INHIBITING THE PROLIFERATION OF BRAIN AND HEPATIC METASTASES BY USING LONIDAMINE

This application continuation of Ser. No. 526,516 filed May 21, 1990, now abandoned a continuation-in-part application of U.S. Ser. No. 783,209, filed Oct. 2, 1985, now abandoned the contents of which are hereby incorporated by reference into the present application.

BACKGROUND OF THE INVENTION

Throughout this application various publications are referenced to by arabic numerals within parenthesis. Full bibliographic citations for these references may be found at the end of the specification immediately preceding the claims. The disclosures for these publications are hereby incorporated by reference into this application to more fully describe the state of the art to which this invention pertains.

One of the active compounds of this invention have been known to the art for some time. Gossypol has the structure:

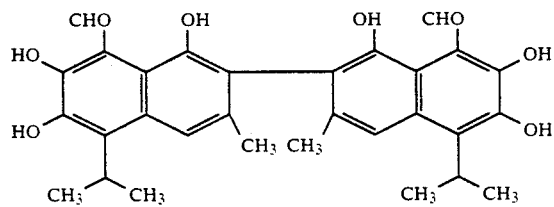

and is known as a yellow pigment obtained from the cotton plant. Primarily, it has been noted as a potential antifertility agent, see e.g., National Coordinating Group on Male Antifertility Agents - cotton phenol (gossypol) in *Clin. Med. J.* 8:455-458 (1980); and *Gynecol. Obstet. Invest.* 10:163-176 (1979). It has been observed as well, that gossypol is selectively toxic to testicular tissues, with no observable effect on other tissues (55, 56, 57). The mechanism of the drug's contraceptive action, its pharmokinetics, and the basis for its toxicological action are not understood.

Recently, cell culture studies have shown that gossypol has anti-tumor effects against cultured tumor cell lines (58, 59, 60, 61). One factor common to tumor cells which were found sensitive to the drug was a high level of lactate dehydrogenase, especially cathodic forms of this enzyme (59). Biochemical studies of gossypol have shown that the principle action of the drug is in inhibition of glycolytic and mitochondrial bound enzymes, with interference of ion transport (58, 62-71).

Rhodamine 123 is a cationic fluorescent dye which binds specifically to mitochondria of living cells (72, 73), and it has been used as a supravital mitochondrial probe for long term cell culture studies. Continuous exposure of cells to rhodamine 123 at high doses, is found to inhibit oxidative phosphorylation, to arrest cells in $G_1$ phase, and to induce loss of reproductive capacity (72, 73, 74). Some further studies of the toxic effect of rhodamine 123 on a variety of cell lines in culture have led to the tentative conclusion that the dye may be selectively cytotoxic against carcinoma cells, probably because of prolonged retention in carcinoma mitochondria (75).

Hyperthermia, or heat treatment of cancer cells, has been a recognized form of cancer therapy for sometime. Briefly, in hyperthermic treatment, cancer cells are treated, locally, with temperatures as high as 42° C. This localized heat treatment is observed to inhibit or to destroy cancer cells with no appreciable harm to normal cells. Systemic hyperthermia, or application of heat to raise the temperature of the body is also used. In this case, care must be taken so that the temperature is not raised above the temperature where normal tissue is destroyed.

Anti-fertility drugs have recently received attention as being useful as hyperthermic sensitizers, i.e., when applied to cancer cells, the compounds tend to increase the efficacy of the heat treatment (24, 76, 77). No work has been done, however, on the effect of gossypol, or rhodamine 123, in the context of hyperthermic sensitivity.

However, in some situations, such as when heating the tumor mass to greater than 42° C. is not feasible because the tumor being treated is deep seated and/or cooled by close opposition to large normal blood vessels, trimodality therapy is able to control tumor masses. For the purposes of this invention, trimodality therapy is defined as therapy encompassing the use of a compound, radiation and heat.

SUMMARY OF THE INVENTION

This invention provides a method of inhibiting the proliferation of cancer cells which comprises contacting the cells with an effective amount of gossypol or rhodamine 123, and applying an effective amount of heat to the cells, effective to inhibit proliferation of the cancer cells.

This invention also provides a method of inhibiting the proliferation of cancer cells which comprises contacting the cells with an effective amount of a compound selected from the group consisting of lonidamine, nicotinamide, gossypol, rhodamine 123 and flunarizine, an effective amount of heat and an effective amount of radiation.

This invention further provides a method of treating a patient having a tumor which comprises administering to the patient an effective amount of a compound selected from the group consisting of lonidamine, nicotinamide, gossypol, rhodamine 123 and flunarizine, applying an effective amount of heat to the tumor and an effective amount of radiation to the tumor.

DETAILED DESCRIPTION OF THE INVENTION

Figure 1:
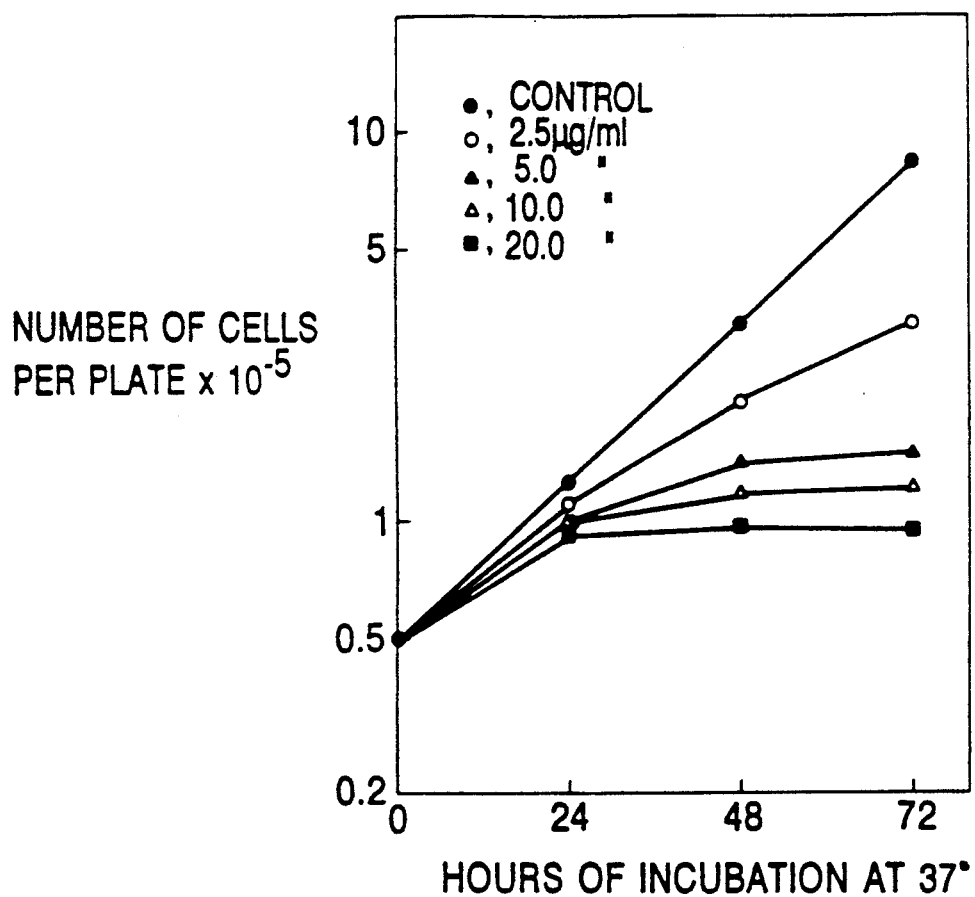
FIG. 1 shows the effect of gossypol on cell multiplication, as a function of time, at a temperature of 37° C.

This invention provides a method of inhibiting the proliferation of cancer cells which comprises contacting the cells with an effective amount of gossypol and applying an effective amount of heat to the cells, effective to inhibit the proliferation of the cancer cells. For the purposes of this invention, the effective amount of gossypol comprises from about 5 $\mu$g/ml to about 20 $\mu$g/ml.

A method of inhibiting the proliferation of cancer cells is also provided by this invention which comprises contacting the cells with an effective amount of rhodamine 123 and applying an effective amount of heat to the cells, effective to inhibit the proliferation of the cancer cells. For the purposes of this invention, the effective amount of rhodamine 123 comprises from about 5 $\mu$g/ml to about 20 $\mu$g/ml.

This invention further provides a method of inhibiting the proliferation of cancer cells which comprises contacting the cells with an effective amount of a compound, an effective amount of heat and an effective amount of radiation, effective to inhibit proliferation of the cancer cells. Compounds useful in the practice of this invention include, but are not limited to a compound selected from the group consisting of lonidamine, nicotinamide, gossypol, rhodamine 123, and flunarizine. In addition, the radiation source useful in the practice of this invention is either photon radiation or electron radiation, and the source will vary with the type of cancer cell being contacted.

The method may be practiced in vitro or in vivo. If the method is practiced in vitro, contacting may be effected by incubating the cells with the compound. The concentration of the compound is the concentration which is effective to inhibit proliferation of the cells and will vary with the type of compound and the type of cancer cell being contacted. Heat and radiation may then be applied to the cells, either concurrently or the radiation may be applied subsequently to the heat.

This invention also provides a method of treating a patient having a tumor which comprises administering to the patient an effective amount of a compound, applying an effective amount of heat to the tumor and an effective amount of radiation to the tumor. Compounds useful in the practice of this invention include, but are not limited to a compound selected from the group consisting of lonidamine, nicotinamide, gossypol, rhodamine 123, and flunarizine. In addition, the radiation source useful in the practice of this invention is either photon radiation or electron radiation. The heat and radiation may be applied concurrently or the radiation may be applied subsequently to the heat.

For the purposes of this invention, it is intended that the compounds be administered as a composition comprising the compound and a pharmaceutically acceptable carrier. As used herein, the term "pharmaceutically acceptable carrier" encompasses any of the standard -pharmaceutical carriers, such as a phosphate buffered saline solution, water, and emulsions, such as an oil/water emulsion, and various types of wetting agents.

The effective amount of heat which is applied to the tumor is an amount which is sufficient to raise the temperature of the tumor cells to above about 38° C. However, it is preferred that an amount of heat be applied which is sufficient to raise the temperature of the tumor cells to above about 41° C. In addition, tumors which are effectively treated with this method are so called "deep-seated" tumors.

Methods of administration to the patient are well known to those of ordinary skill in the art and include, but are not limited to administration orally, intravenously or parenterally. Administration may be effected prior to radiation or hyperthermia, or continuously or intermittently throughout the other treatments.

The amount of the compound administered to the patient is the amount which is effective to inhibit the proliferation of the tumor and effectively treat the patient. Methods of determining the effective amount of the compound are well known to those of ordinary skill in the art and will vary with the type, size and number of lesions being treated and may be determined from published tolerance data.

However, when the compound is lonidamine, it is preferred that it be administered orally at from about 100 mg t.i.d. to about 200 mg t.i.d., and preferably at about 150 mg t.i.d. or at a dosage of about 25 mg/kg/day to about 200 mg/kg/day, preferrably at 50 mg/kg/day. The compound should be administered beginning 3 days prior to the radiation/hyperthermia treatments. When the compound is nicotinamide, it is preferred that it be administered orally on all radiation treatment days in a single dose of about 1 gm to about 5 gm, preferably at 3 grams, or in a dosage of about 100 mg/kg/dose to about 600 mg/kg/dose. It is also preferred that it administered to the patient just prior to initiating hyperthermia and approximately one (1) hour prior to that day's radiation treatment.

Methods of heating tumors locally are also well known to those of skill in the art, for example, when the patient has individual lesions which may be less than 3 cm in diameter, and total fields less than 10 cm in diameter, the patient may be treated with the Magnather TM 27 MHz RF inductive hyperthermia unit; patients with a deep seated lesion, total field greater than or equal to 10 cm, and individual lesions $\geq 3$ cm in diameter, may be treated with the Thermatron TM RF-8 capacitive hyperthermia unit. When heating deep seated lesions, appropriate bolus pads may be employed with skin cooling as needed to prevent local injury.

Hyperthermic treatment may be given weekly or twice weekly. In the preferred embodiment of this invention, the patient receives hyperthermic treatment on a twice weekly basis, just prior to that day's radiation therapy. In addition, it is preferred that the goal of the heating be to reach a maximum temperature of 42° C. within the periphery of the tumor. The temperature should be held for about 30 minutes to about 90 minutes, with the preferred time limit to be about 60 minutes. The intensity of the heating should be adjusted to the patient's tolerance and subcutaneous and skin temperatures and should be monitored so that they do not exceed 42° C.

Radiation therapy is initiated after hyperthermic treatment and preferably within 15 to 30 minutes after the conclusion of hyperthermia. The tumor dosage delivered will be from about 15 to about 50 Gy in previously irradiated tumors With the preferred dosage comprising about 25 to about 35 Gy. In previously unirradiated lesions, the tumor dosage delivered will be slightly higher, i e., up to about 65 Gy, with the preferred dosage Comprising about 35 to about 45 Gy. Radiation will be administered 5 days/week, in fractions of about 2 Gy. On those days when both hyperthermia and radiation therapy are administered, the radiation should be administered after hyperthermic treatment. The specific radiation modality to be used, i.e., photons versus electrons, is dictated by the anatomical location of the lesion(s) being treated, and is well known to those of ordinary skill in the art.

It is to be understood in the following disclosure that hyperthermic treatment refers to localized and systemic treatment of the patient.

EXPERIMENTAL METHODS

Gossypol Experiments

Experiments were carried out with HeLa S-3 cells grown in Eagle's minimal essential medium supplemented with 10% fetal calf serum.

Plated monolayer cells were heated within 0.05° of the desired temperature by totally immersing plastic culture flasks in a heated water bath. Water bath temperatures were verified by a National Bureau of Standards thermometer.

The pH of the culture medium was adjusted by varying the $CO_2$ content of the gas phase within the flasks. The buffering system of Eagle's minimal essential medium consisted of 26 mM $NaHCO_3$ at 5% $CO_2$ for neutral pH of 7.4. To obtain a pH of 6.7, for example, the flasks were flushed with the gas mixtures containing 26% $CO_2$. The pH of the culture medium was monitored throughout the treatment procedures by sealing a combination electrode in a treatment vessel and monitored with temperature-compensated digital pH meter.

The "glucose-deprived" medium was prepared by adding 10% dialyzed fetal calf serum to the culture medium without glucose. The dialyzed fetal calf serum contained less than 1 mg glucose per 100 ml so that the final concentration of glucose in the "glucose-deprived" medium was less than 0.001 mg per ml.

Gossypol was dissolved in DMSO immediately prior to experiments. DMSO produced no enhancement of hyperthermic cytotoxicity with the range studied.

Effect of Gossypol on Cell Multiplication

Preliminary experiments were carried out to determine the effect of gossypol on cell division. Exponentially growing HeLa cells were exposed to the drug for 72 hours at 37° C. Control cells grew exponentially with a doubling time of approximately 19 hours. Cells exposed to drug concentrations of 5, 10 and 20 µg/ml grew exponentially for the first 24 hour period and then remained stationary. The growth curve of cells treated at a gossypol concentration of 2.5 µg/ml was not significantly different from the control for the initial 24 hours incubation; however, at incubation times greater than 24 hours, a lengthening of doubling time was observed (FIG. 1). The growth rate of the cells exposed to 1.25 µg/ml was the same as that of the control cells.

Effect of Gossypol on Cell Survival at Elevated Temperature

Figure 2:
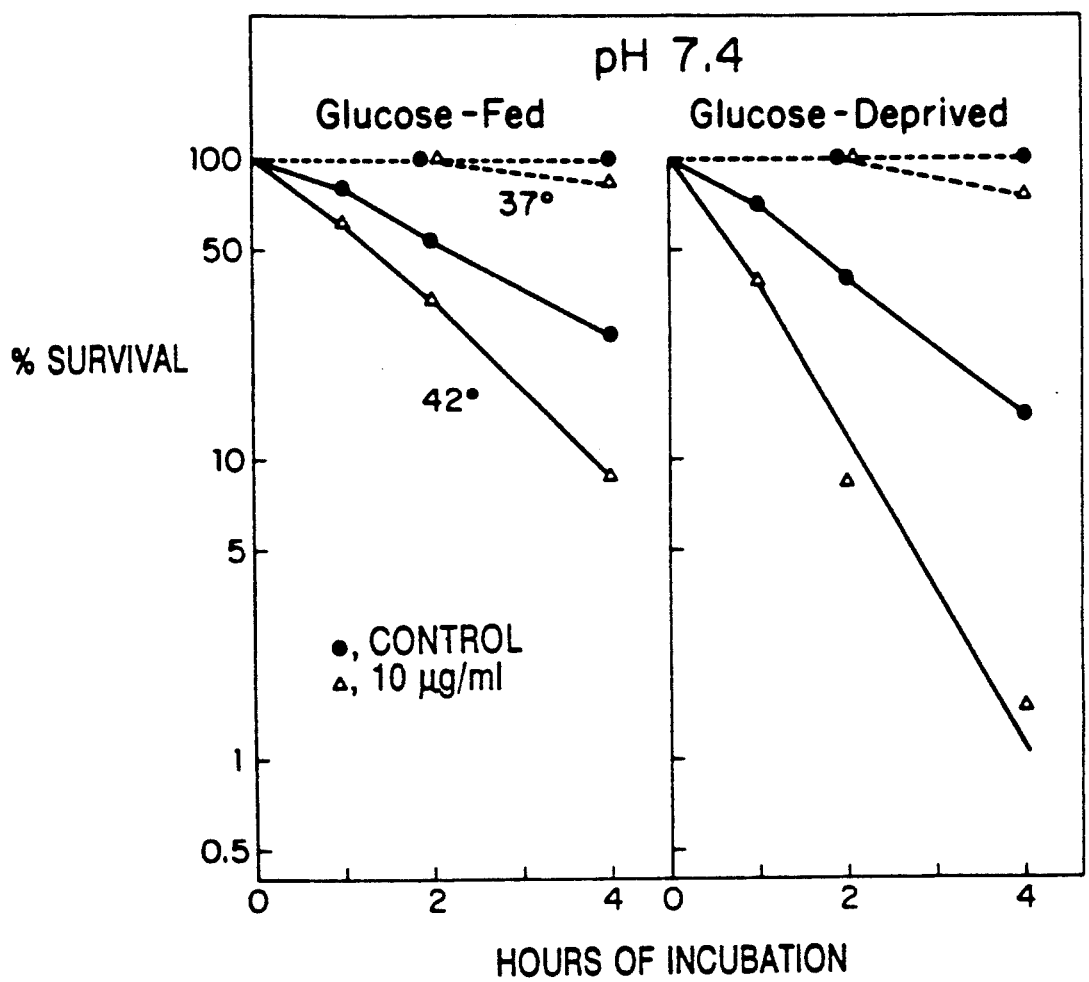
FIG. 2 shows gossypol's effect, during heating, at different pH levels.
Figure 3:
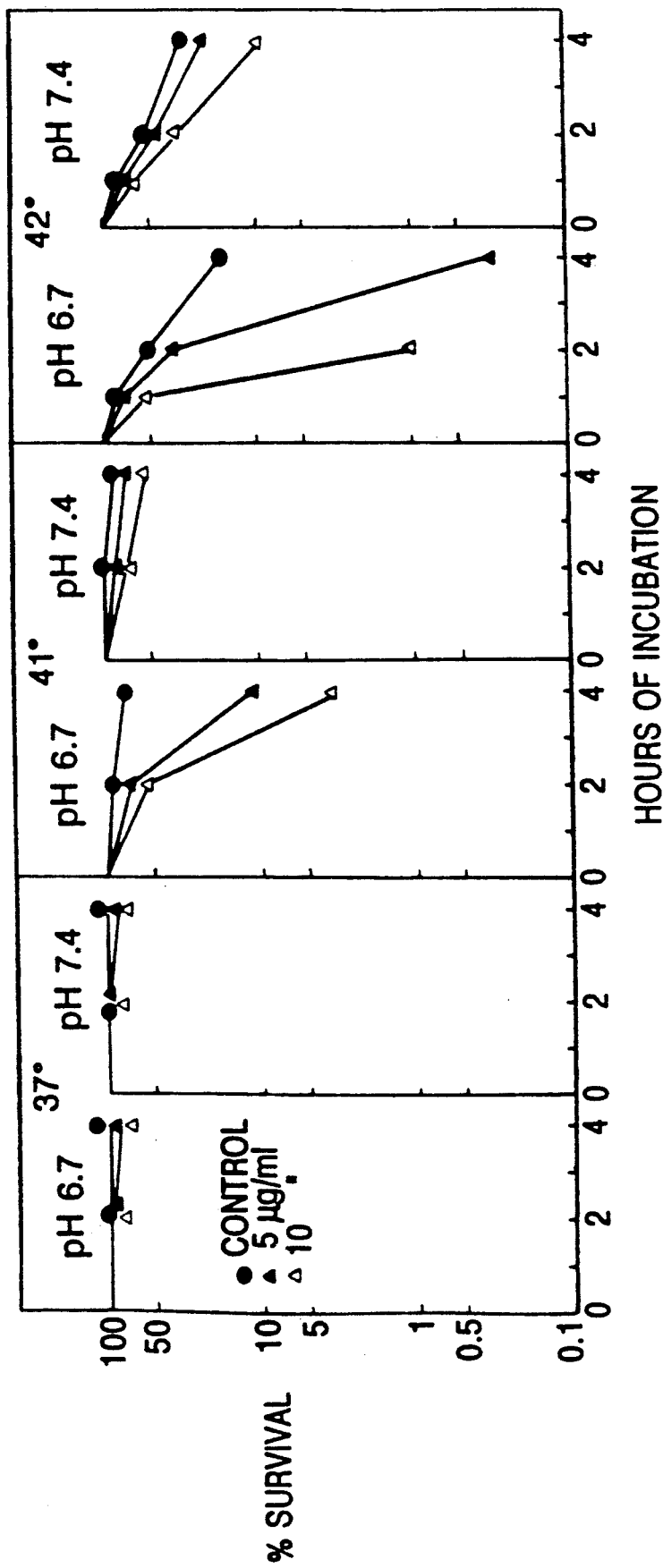
In FIG. 3, survival rate is shown as a function of gossypol concentration, for cells at 42° C. for two hours, under acidic or neutral pH conditions.

FIG. 2 shows the survival curves of cells as a function of exposure time under various pH conditions and drug concentrations. The survival curves of cells incubated at 37° C. with 5 and 10 µg/ml of gossypol for up to 4 hours shows no appreciable drug toxicity under acidic or neutral conditions. Since the drug concentrations and exposure time of 4 hours did not show any detectable toxicity at 37° C., these treatment conditions for the subsequent studies at elevated temperatures was selected. It is apparent that the cytotoxic effect of hyperthermia on drug-tested cells was most pronounced under acidic conditions. The dose-dependent effect of the drug is clearly shown in FIG. 3. For example, at 10 µg/m. and 2 hours exposure at 42° C., the cells survival is reduced to 1% under acidic condition. Heat treatment alone reduces the cell survival to only 50% of the control.

Effect of Gossypol on Glucose-Deprived Cells

Figure 4:
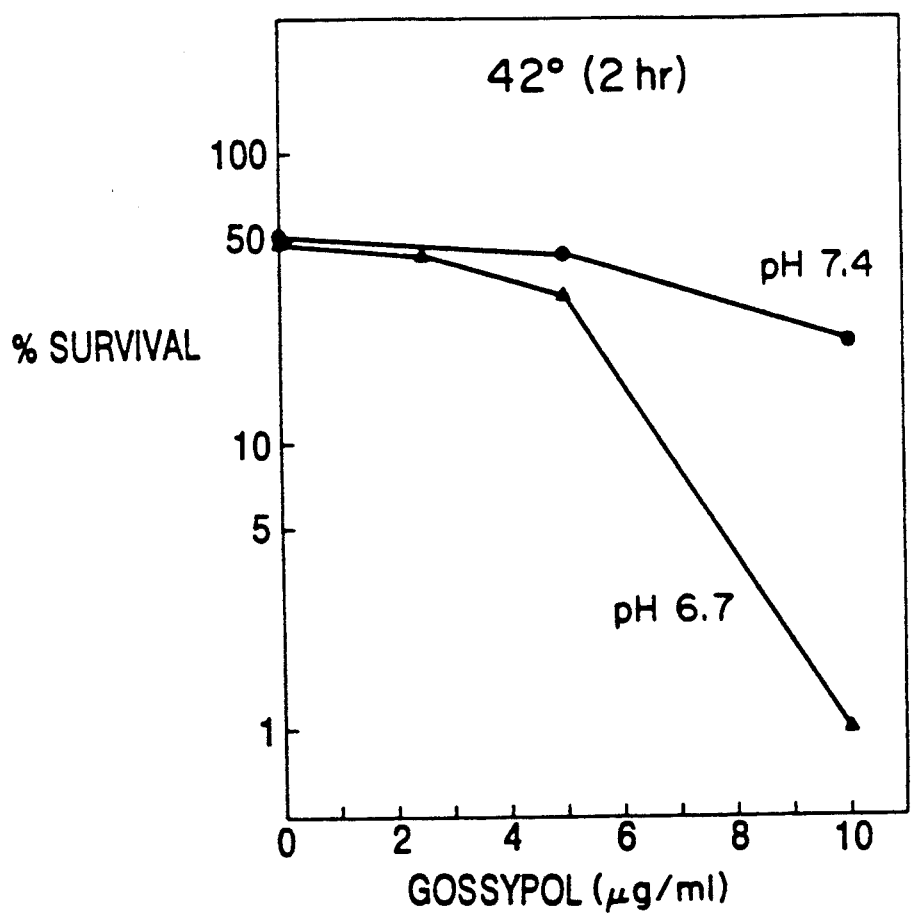
FIG. 4 shows the effect of gossypol on glucose deprived cells.

Since gossypol has been reported to interfere with cellular energy metabolism, experiments were performed to determine the influence of glucose on the cytotoxic effect of gossypol. FIG. 4 shows the results of experiments under glucose-fed and glucose-deprived conditions at pH 7.4. Incubation at 37° C. with 10 µg/ml gossypol for hours under glucose deprivation produced no apparent cytotoxicity. However, when these cells were heated at 42° C. for 4 hours with 10 µg/ml gossypol, a substantial increase in cell killing was seen in glucose-deprived cells. The survival of glucose-fed cells exposed to the same treatment was approximately 10% while that of glucose-deprived cells can further enhance the cytotoxic effect of gossypol at elevated temperature.

Rhodamine Experiments

Experiments were carried out with HeLa S-3 cells grown in Eagle's minimal essential medium supplemented with 10% fetal calf serum. Details of the cell culture procedures including the maintenance, the trypsinization, and the test for contamination of cultures with mycoplasma were described elsewhere (Kim et al. Cancer Res. 44:102-106 (1984); Kim et al. Cancer Res. 38:2935-2938 (1978)). No antifungal agent was used.

Cell survival was assayed by colony-forming ability of plated single cells to obtain quantitative dose-survival curves. Details of cloning experiments including colony court have been described elsewhere (See, e.g., Kim et al. supra).

Plated a synchronous monolayer cells were heated to within 0.05° C. of the desired temperature by totally immersing plastic culture flasks in a water bath. Water bath temperatures were verified by a National Bureau of Standards calibrated thermometer.

The pH of the culture medium was adjusted by varying the $CO_2$ content of the gas phase within the flasks. The buffering system of Eagle's minimal essential medium consisted of 26 mM $NaHCO_3$ at 5% $CO_2$ for neutral Ph of 7.4. To obtain pH of 6.7, for example, the flasks were flashed with the gas mixtures containing 26% $CO_2$. The pH of the culture medium was monitored throughout the treatment procedures by sealing a combination electrode in a treatment vessel and monitored with a temperature-compensated digital pH meter.

The "glucose-deprived" medium was prepared by adding 10% dialyzed fetal calf serum to the culture medium without glucose. The dialyzed fetal calf serum contained less than 1 mg glucose per 100 ml so that the final concentration of glucose in the "glucose-deprived" medium was less than 0.001 mg per ml.

Rhodamine 123 was dissolved in the minimal essential medium immediately prior to each experiment.

Effect of Rhodamine 123 on Cell Survival at 37° C.

Figure 5:
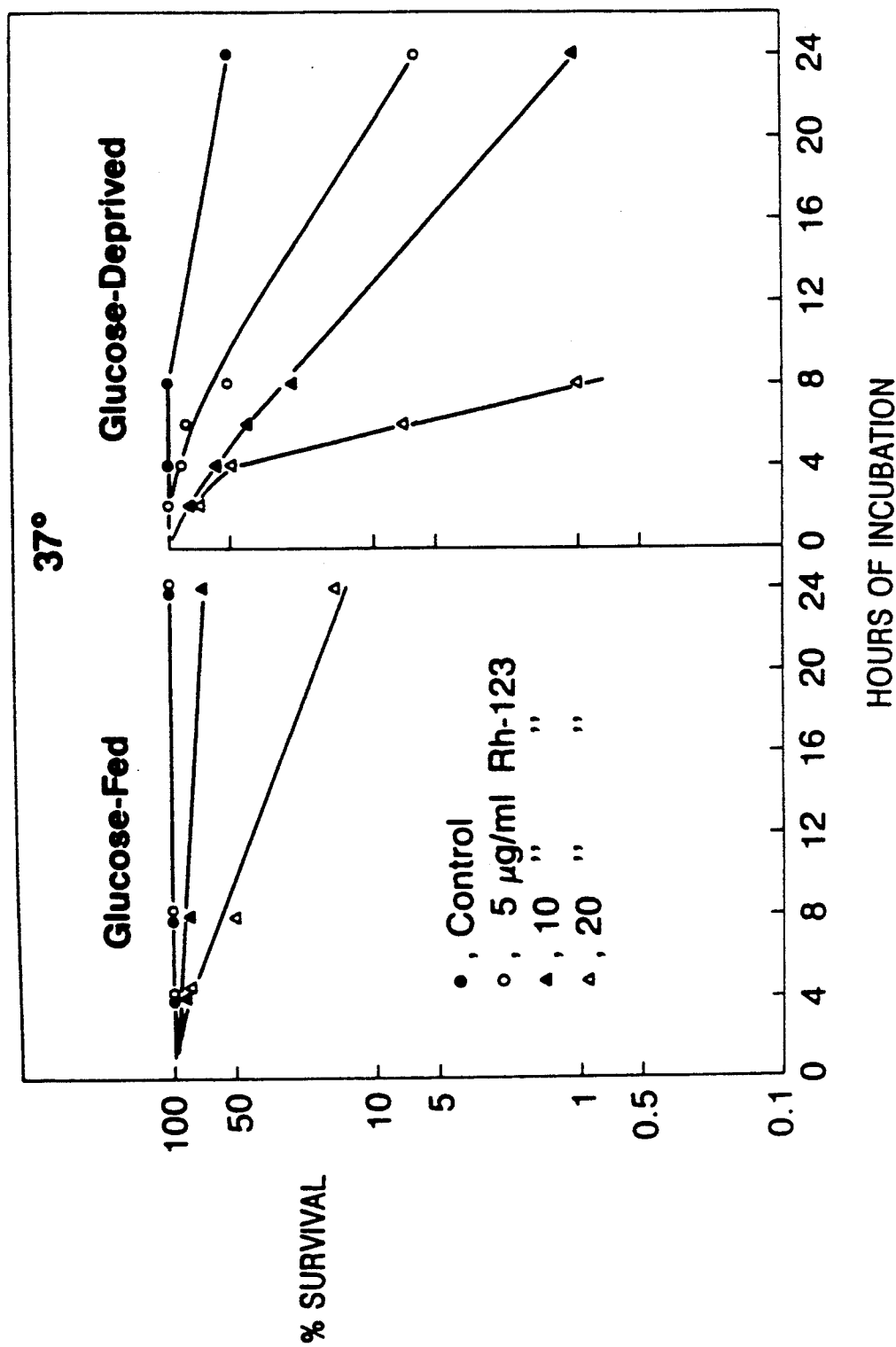
FIG. 5 shows the percent of cell survival, as a function of time exposure to rhodamine 123, in the presence or absence of glucose in the medium.

Prior to the hyperthermia study, experiments were carried out to determine the toxicity of rhodamine 123 on HeLa cells in the presence or absence of glucose in the medium at 37° C. At the initial 4 hour exposure of cells to the compound at 10 μg/ml, there was no appreciable reduction in the cell surviving fraction in either glucose-fed or glucose-deprived cells. When the exposure was extended to 24 hours, there was a significant differential cytotoxicity observed between the glucose-fed and glucose-deprived cells. The surviving fraction of cells treated at 10 μg/ml for 24 hours in the presence of glucose was 0.8, while the surviving fraction in the absence of glucose was less than 0.01. This is shown in FIG. 5.

Effects of Rhodamine 123 on Cell Survival Following Hyperthermia

Figure 6:
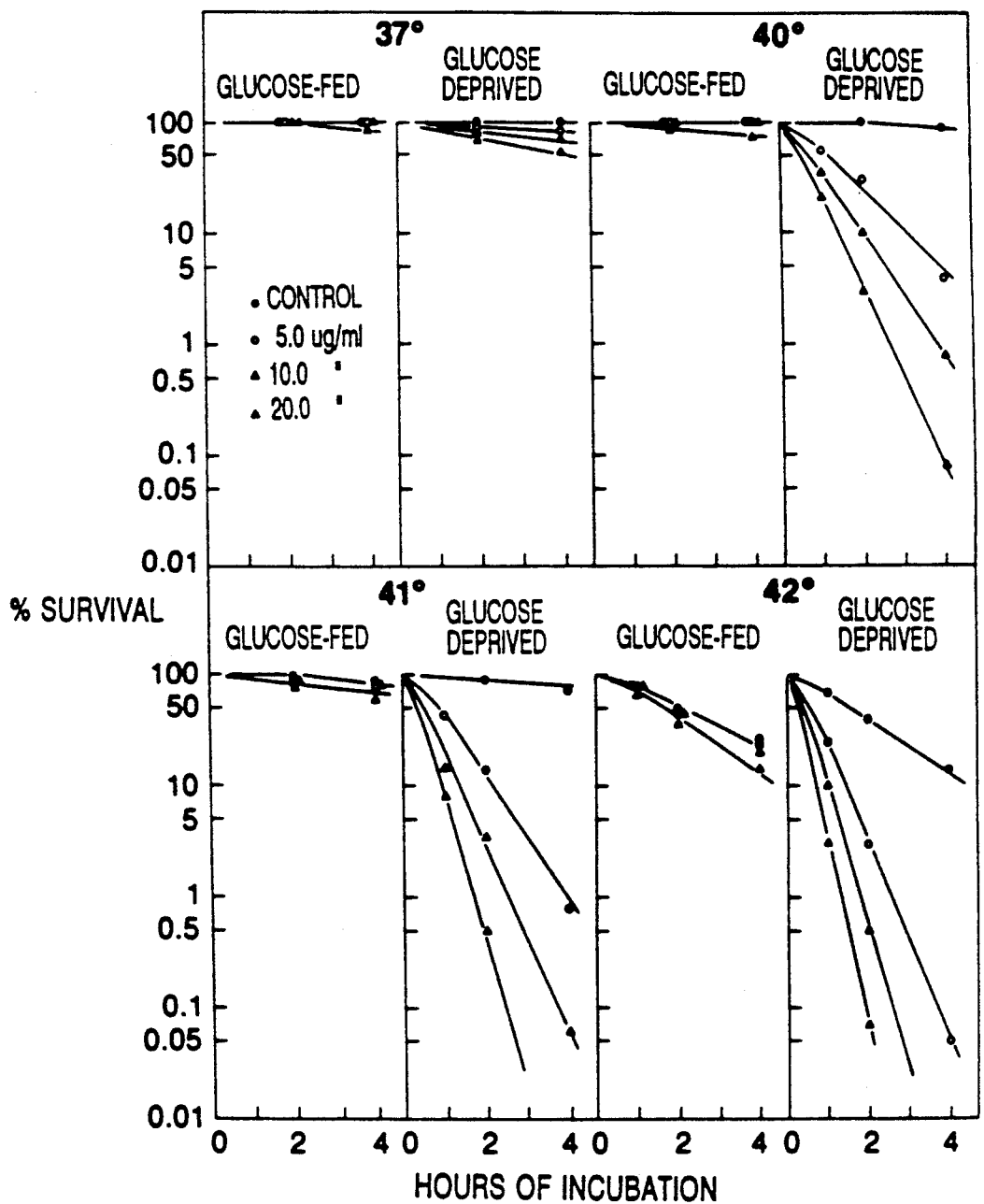
FIG. 6 shows the percentage of HeLa cells which survive, following incubation with various concentrations of rhodamine 123 at temperatures ranging from 37° C. to 42° C., for 0 to 4 hours in the presence or absence of glucose.
Figure 7:
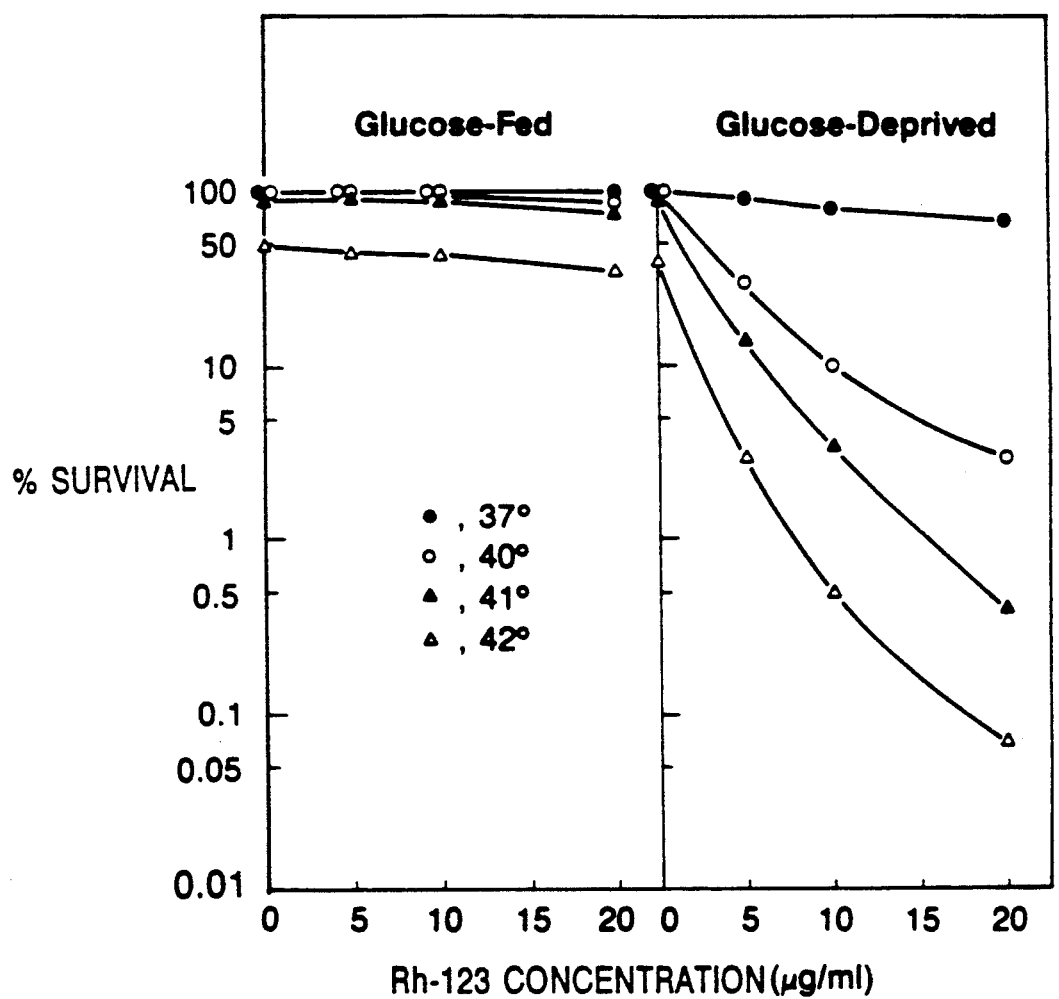
FIG. 7 shows percentage of cell survival of glucose fed and glucose deprived HeLa cells, when exposed to different temperatures for two hours, as a function of rhodamine 123 in culture media.

FIG. 6 shows cell survival curves as a function of exposure time at 40, 41 and 42° C. and drug concentrations. Both the drug concentration and the exposure time limits of 4 hour were chosen, as this treatment at 37° C. did not produce any detectable reduction in cell survival. It was apparent that rhodamine 123 selectively increased the cytotoxic effects of hyperthermia in glucose-deprived cells relative to glucose-fed cells (FIG. 6). FIG. 7 clearly shows that the potentiation of the heat affects was dependent on the elevated temperature and drug concentration in glucose-deprived cells. No hyperthermia enhancement by rhodamine 123 was seen in glucose-fed cells.

Figure 8:
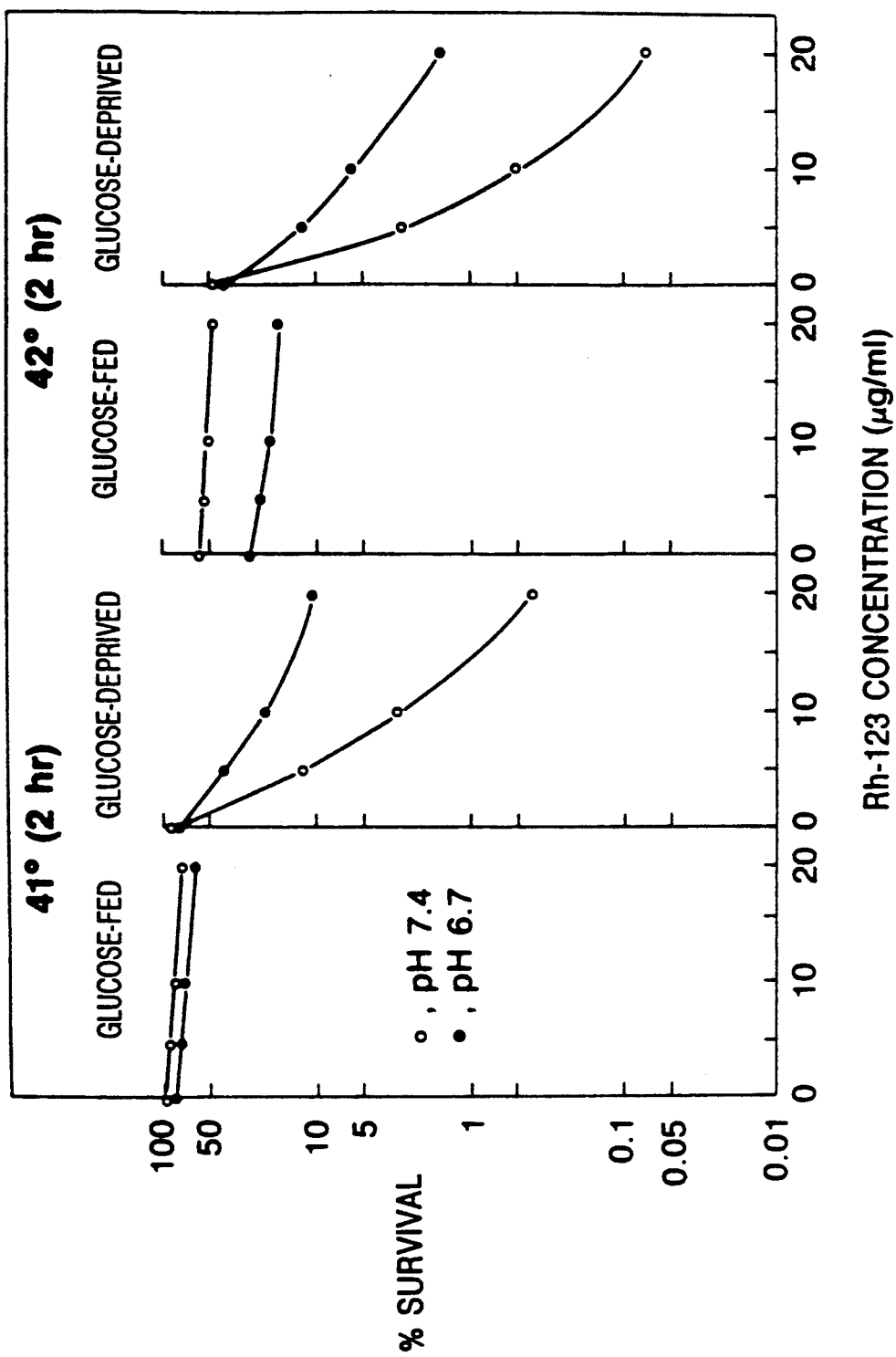
FIG. 8 shows the effect of pH on cell survival as a function of rhodamine 123 concentration in the presence or absence of glucose in the medium.

Since acidic pH is known to increase the cytotoxic effect of hyperthermic treatment, the influence of pH and rhodamine 123 on cell survival following hyperthermia was determined. FIG. 8 demonstrates that the acidic pH did not substantially enhance the cytotoxicity of heat in glucose-deprived cells. Instead, the cytotoxicity was less than that observed at pH 7.4.

These experiments show that both gossypol and rhodamine 123 are effective hyperthermic sensitizers of human cancer cells. In particular, when heated cells are exposed to the combination of gossypol and low pH, or gossypol and glucose deprivation, cell sensitivity increases. Rhodamine 123 has been shown to increase hyperthermic cytotoxicity of cancer cells especially when the cells are deprived of glucose. FIG. 2-4, 6 and 7 show these results graphically.

One possible explanation for the effect of both gossypol and rhodamine 123 may be the role of these compounds in cellular energy equilibrium. If, as is supposed, gossypol uncouples oxidative phosphorylation reactions, the cells would evidence reduced ATP production, with energy depletion and increased sensitivity. When subject to glucose deprivation, ATP production would be blocked in its entirety. Rhodamine 123 may have the same effect, perhaps because of prolonged retention of the compound by mitochondria of transformed cells, as compared to normal cells. This, however, is just one suggestion as to the operating mechanism, and the inventors do not bind themselves to this or any other theory as to the operation of this mechanism.

Hence, the compounds gossypol and rhodamine 123 show efficacy in vivo hyperthermic treatment of cancer cells. Compositions containing the effective amounts of either of these compounds, optionally in combination with suitable carriers or other therapeutic agents which are pharmaceutically acceptable can be used in treating cancer. Similarly, the compounds themselves may be applied to the cancer cells, either with or without carriers or other compounds. The treatment regimen, including frequency of administration, dosage, means of administration, and so forth, will of course vary from patient to patient, depending upon other pertinent factors such as degree of malignancy, age, general health, and so forth. Application of the gossypol or rhodamine 123 can be made in any standard form, including oral, intravenous, intramuscular, or topical administration. Pills, liquids, intravenous fluids, creams, unguents, and so forth, are some of the forms the compounds and compositions may take. All possible regimens, including any and all means of treatment, are encompassed by this invention.

Hyperthermia Effects in Model Systems

As previously stated, temperature elevation to 42° C. produces cytotoxic effects both in cell culture systems and in vivo; energy impaired cells display great sensitivity to hyperthermia, as do cells under acidic media conditions which presumably place increased energy demands upon the cell (9-13). The pH selectivity of hyperthermic effects may provide selectivity for that treatment modality in those tumors which have an acidic interstitial milieu. Hyperthermia must be given intermittently because cells surviving sublethal heating develop resistance to damage from further heating that persists for 48 to 72 hours. Hyperthermia produces enhancement of radiation induced injury to cells in culture and tumors in vivo, provided the two treatments are given in close temporal proximity one to another.

The precise mechanisms of hyperthermic cytotoxicity, and of thermal enhancement of radiation injury have not been established; the elevated temperature increases general cellular energy demands and probably reduces the cell's capacity to perform specific energy requiring tasks, including repair of radiation damage to cellular DNA. When employed in vivo, hyperthermic effects upon tumor blood flow might contribute either to an increased or decreased tumor oxygen content. Recently, it was demonstrated moderate hyperthermia (41° C.) to produce moderate radiation enhancement in a hypoxic mammary tumor, an effect that was not seen in a well oxygenated Meth A fibrosarcoma.

Clinical Studies of Hyperthermia and Radiation Therapy

Using RF inductive heating in paired superficial lesions in 38 patients with malignant melanoma, Kim et al. demonstrated combined hyperthermia and radiation therapy to be superior to radiation therapy, producing a 75% versus 46% local tumor control rate ($P<0.01$) (14). This favorable effect has been confirmed by multiple workers in a variety of tumors (15-18). The superiority of the combined therapy was particularly evident in larger lesions where radiation alone had negligible effect (14 and 18).

Nicotinamide as a Radiation Sensitizer

Jonsson et al. observed nicotinamide to have radiation enhancing effects in mice bearing the transplanted C3H mammary adenocarcinoma (19). The work was confirmed and extended by Horsman et al. in the EMT-6, Lewis Lung. and RIF-1 tumors; optimal results were obtained by injecting the drug 1 to 3 hours prior to radiation treatment (20-21). Plasma levels of nicotinamide ranged from 3 to 7 mM at the time of radiation. This was recently confirmed in the transplanted mechanism CA murine mammary adenocarcinoma, a well characterized hypoxic tumor, and extended them to examine nicotinamide as an enhancing agent in trimodality therapy. The combination of nicotinamide (0.5 gm/kg), given 1 hour prior to radiation therapy, and mild hyperthermia (41° C. for one hour), just prior to radiation therapy produced significant enhancement of the effect of radiation therapy with a radiation dose modification factor of 1.77. Bimodality therapy with hyperthermia and radiation yielded a DMF of 1.36; the DMF for nicotinamide plus radiation (without hyperthermia) was 1.35 (22).

The mechanism by which nicotinamide produces radiation enhancement is not established. It is active against this hypoxic murine tumor but inactive against the oxic Meth-A fibrosarcoma model (22), suggesting that it might be increasing tissue oxygen tension, either by inhibiting respiration, or by producing vasodilatory effects. However, nicotinic acid, which has established vasodilatory effects, did not produce radiation enhancement in the MCA mammary tumor system even at the $LD_{10}$ dosage. Nicotinamide is an inhibitor of poly-ADP ribose synthetase, an essential enzyme in DNA excision repair; however, in our hands, nicotinamide is not active in cell culture models and activity at this level would be inconsistent with its inactivity in the well oxygenated Meth-A fibrosarcoma system. Regardless of the mechanism, the drug is quite active and non-toxic in mice at the optimal dose of 0.5 gm/kg (1.5 gm/m$^2$); the extensive experience with nicotinamide in the treatment of schizophrenia indicates that comparable plasma levels can be readily achieved in humans, where daily doses of 6 gm daily (3 to 4 gm/m$^2$) were found to be safe and associated with only a low incidence of side effects (23).

Lonidamine Enhancement of Radiation and Hyperthermia in Model Systems

Lonidamine, 1-(2,4-dichlorophenyl)IH-indazole-3-carboxylic acid, a potent inhibitor of spermatogenesis in mammals, is a radiation and hyperthermia enhancing agent in cell culture and murine tumor systems (24-26). It has inhibitory effects on both oxidative and glycolytic metabolism of mammalian cells (27,28). Its hyperthermia enhancing effects are greatly increased by acidification of the cell culture medium (24); it is an inhibitor of repair of radiation-induced potentially lethal damage (PLD) (29,30). In many of its effects in model systems lonidamine is closely similar to gossypol, another inhibitor of spermatogenesis that acts by way of effects on glycolytic metabolism (31). Recent work by Kim et al. (30) in a multicellular HeLa spheroid system demonstrated that the effect of the lonidamine was increased by fractionation of the radiation dose; moreover, the data suggested that cells which received the combined treatment had undergone a metabolic change, such that their sensitivity to growth inhibitory effects of lonidamine was increased. Based on these studies, and on supportive studies in mice receiving the drug chronically, Kim et al. proposed that optimal use of lonidamine would be to employ it both during and, in a prolonged exposure, after the course of radiation therapy. This concept was reflected in current clinical trials with the agent, including a placebocontrolled randomized study in patients with head and neck cancer where lonidamine significantly increased the disease free survival rate produced by radiation therapy (32).

Rationale for Trimodality Therapy

Cell culture studies have shown that the thermal enhancement ratio is greatly increased, with three combined modalities relative to just combined heat and radiation (33); the in vivo data with lonidamine and nicotinamide support the concept as well (22, 34); thus, the following theoretical analysis may be pertinent to the observed increase in therapeutic effect. Because the different modalities employed have their maximal effect on differing populations within tumors, a population that is refractory to one modality may be at increased risk to cytotoxic damage from the second or third. For example: 1) The steady state tissue temperature achieved from local external heating results from the balance of heat delivered and heat removed by blood flow; since the truly hypoxic areas will have poor blood flow, their heating will be more effective and their temperature higher. 2) Hyperthermic cytotoxicity is not affected by the cell's oxic or hypoxic status; therefore, the increased temperature in hypoperfused areas should result in significant cell kill. 3) The tumor cell population in hypoperfused areas may be relatively non-proliferative because of its nutritionally deprived state; accordingly, it would be radioresistant on a cell kinetic basis as well as on the basis of hypoxia. However, hypoperfused areas are also commonly acidic; therefore, the acidic pH thermosensitizers (lonidamine and gossypol) may potentiate the cytotoxic effects of hyperthermia in these (radioresistant) cell populations. 4) Although the well perfused areas in tumors are heated poorly, they are well oxygenated and on that basis relatively accessible to radiation injury; moreover, the inhibition of potential lethal damage repair induced by lonidamine can enhance radiation effect in this population as well.

Studies on Nicotinamide

Figure 9:
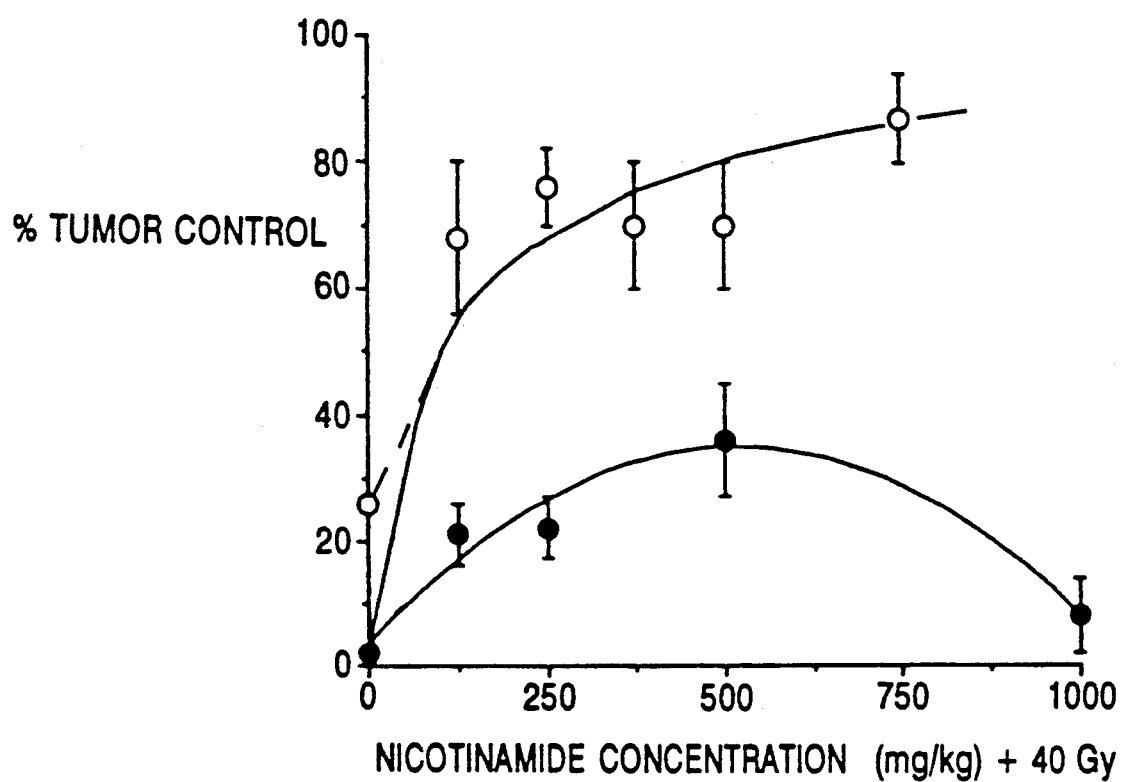
FIG. 9 shows percent local tumor control of the CBU-MCA mammary carcinoma following a single dose of 40 Gy radiation as a function of the nicotinamide concentration, with and without concomitant hyperthermia (41° C. for 1 hour).
Figure 10:
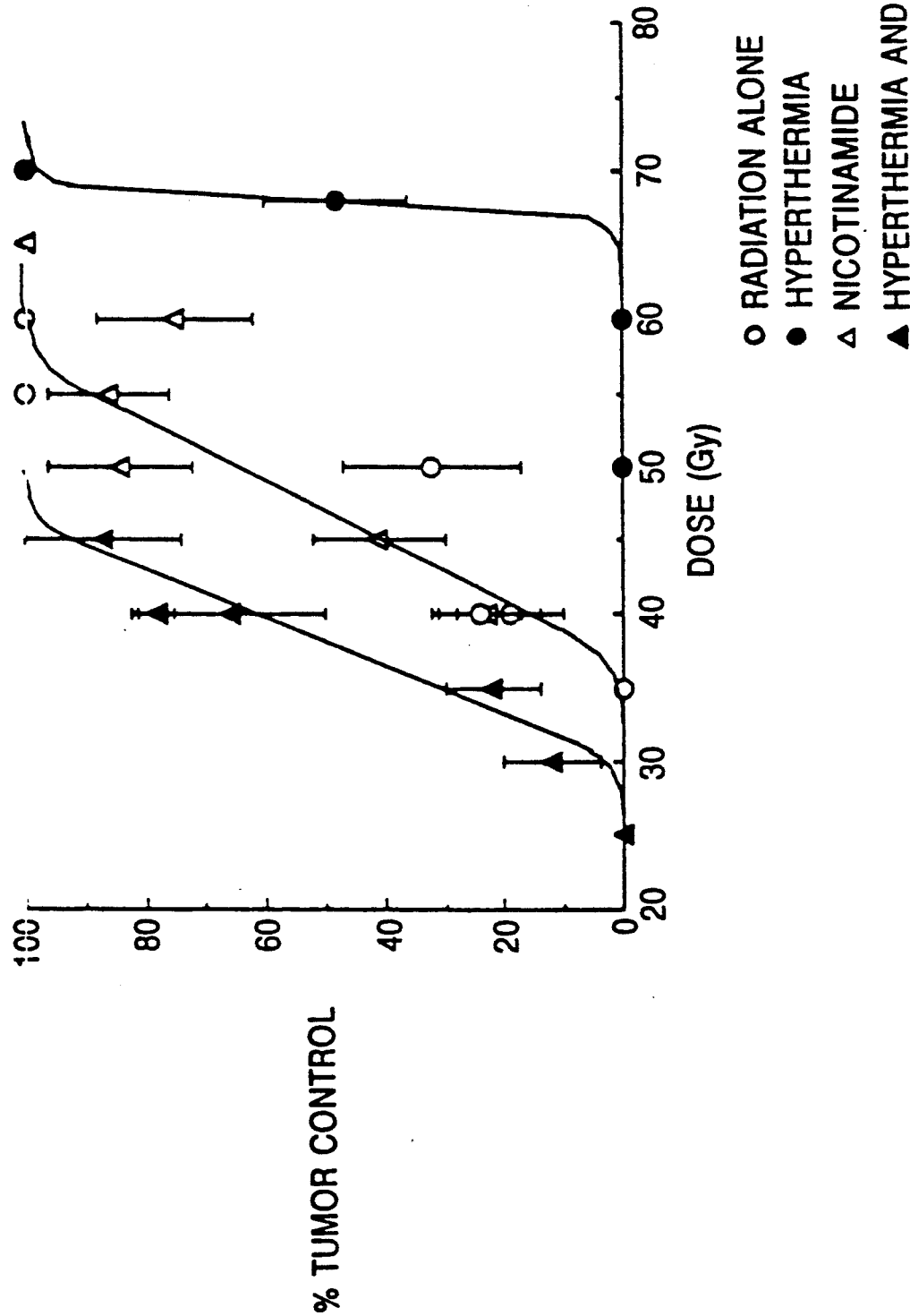
FIG. 10 shows the percent local tumor control of the CBU-MCA mammary carcinoma as a function of single dose X-irradiation. Nicotinamide was administered intraperitoneal one (1) four before irradiation. Localized mild hyperthermia (41° C.) was applied for one (1) hour immediately prior to irradiation.

No radiation enhancement was obtained in cell culture experiments with nicotinamide concentrations <10 mM; in contrast, when nicotinamide was administered i.p. in a dosage of 125 to 500 mg/kg, one hour prior to irradiation and immediately prior to 1 hour heating at 41° C., it produced clear enhancement of the effects of radiation and radiation plus hyperthermia in the MCA-mammary carcinoma, a hypoxic murine model tumor. (22) See FIGS. 9 and 10. As noted previously, the following DMF's were obtained for the respective experimental conditions: Nicotinamide+Radiation Therapy=1.36, Hyperthermia+Radiation Therapy=1.36, Nicotinamide+Hyperthermia+Radiation Therapy=1.64. In contrast with these results with the hypoxic and radioresistant MCA-mammary carcinoma, nicotinamide therapy produced no radio-enhancing effect in the oxic and radiosensitive Meth-A fibrosarcoma (22).

Studies on Lonidamine

Figure 11:
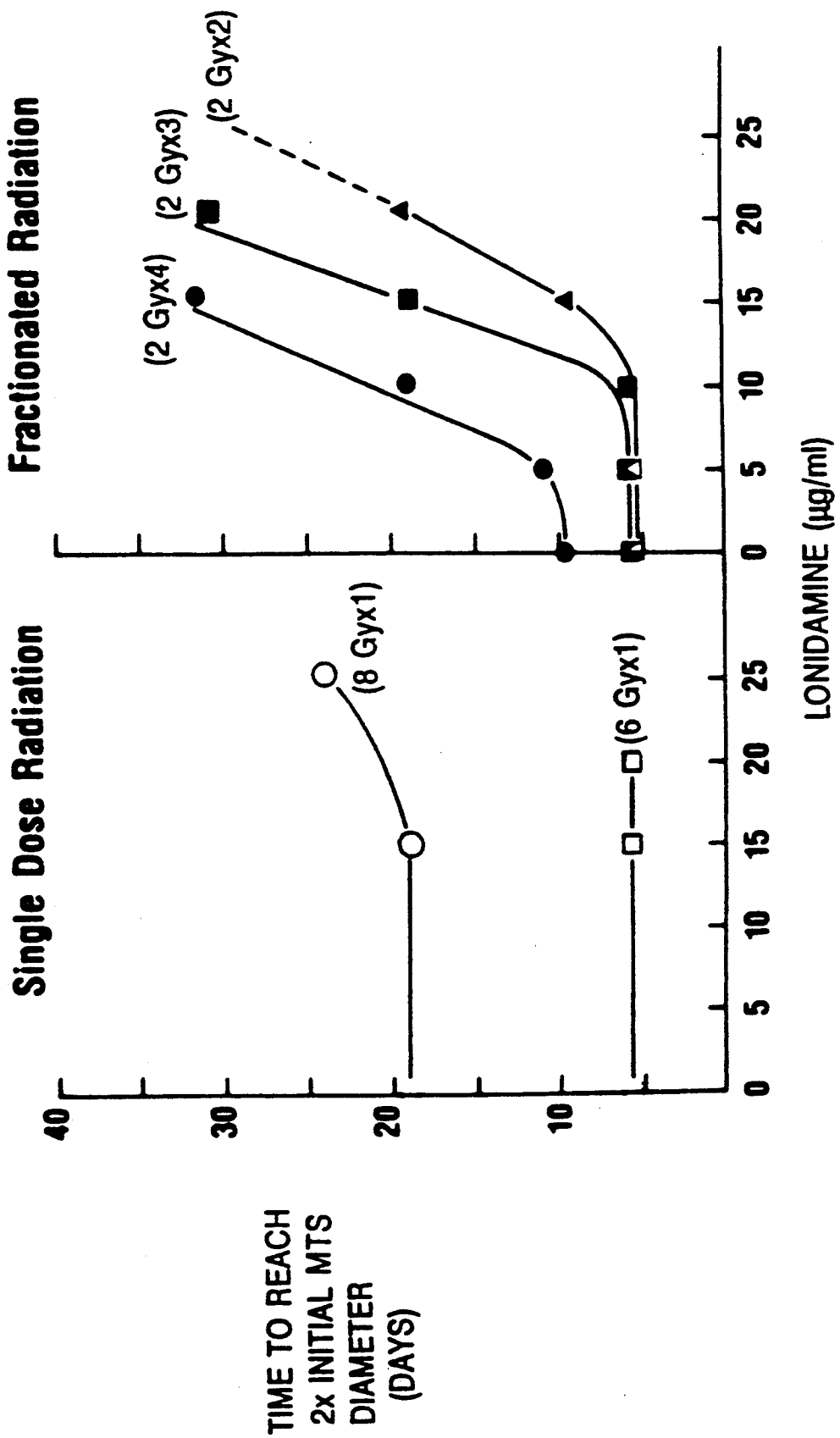
FIG. 11 shows lonidamine-induced enhancement of radiation therapy, which is increased with increasing dose fractionation.
Figure 12:
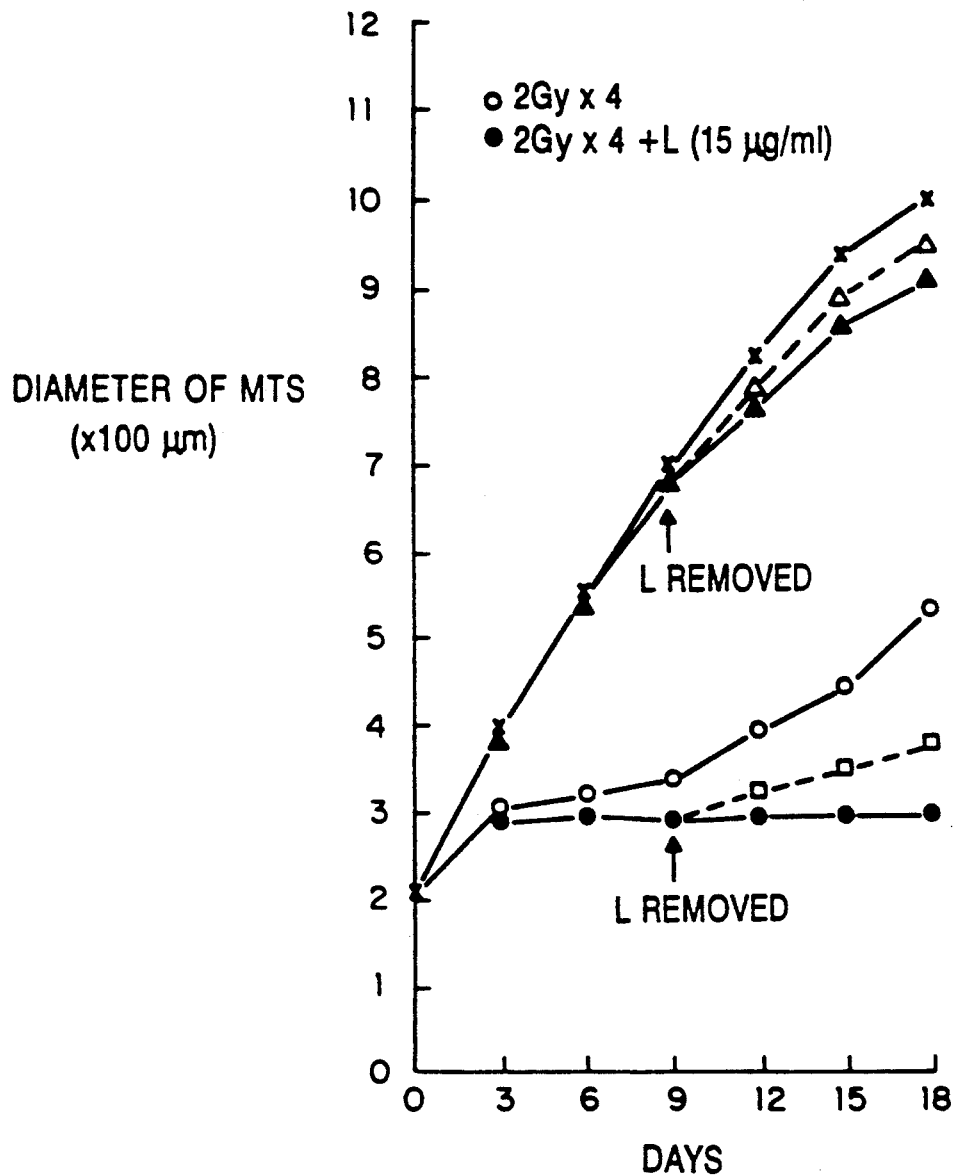
FIG. 12 shows the effect of lonidamine removal on the growth rate of irradiated multicellular tumor spheroids.

Lonidamine produces enhanced cytotoxic effects in cells treated either with radiation or hyperthermia (24–26); it is an established inhibitor of repair of potential lethal damage (29,30). Although the mechanisms have not been fully elucidated, lonidamine does perturb energy metabolism in neoplastic cells (27,28); its effects are increased in cells under conditions of reduced extracellular pH (24). The drug's radio-enhancing effects in multicellular tumor spheroids (MTS) was examined assessing growth delay following radiation with and without the drug. Consistent with its inhibitory effects on potential lethal damage, the observed lonidamine-induced enhancement of radiation therapy . effect is increased with increasing dose fractionation (FIG. 11) (30); moreover, since the MTS begins to grow again when lonidamine is removed 5 days following the last radiation exposure, radiation therapy itself appears to sensitize cells to the inhibitory effects of lonidamine (FIG. 12) (30), because of these considerations, in clinical use the drug is currently being administered chronically both during and subsequent to the course of radiation.

Figure 13:
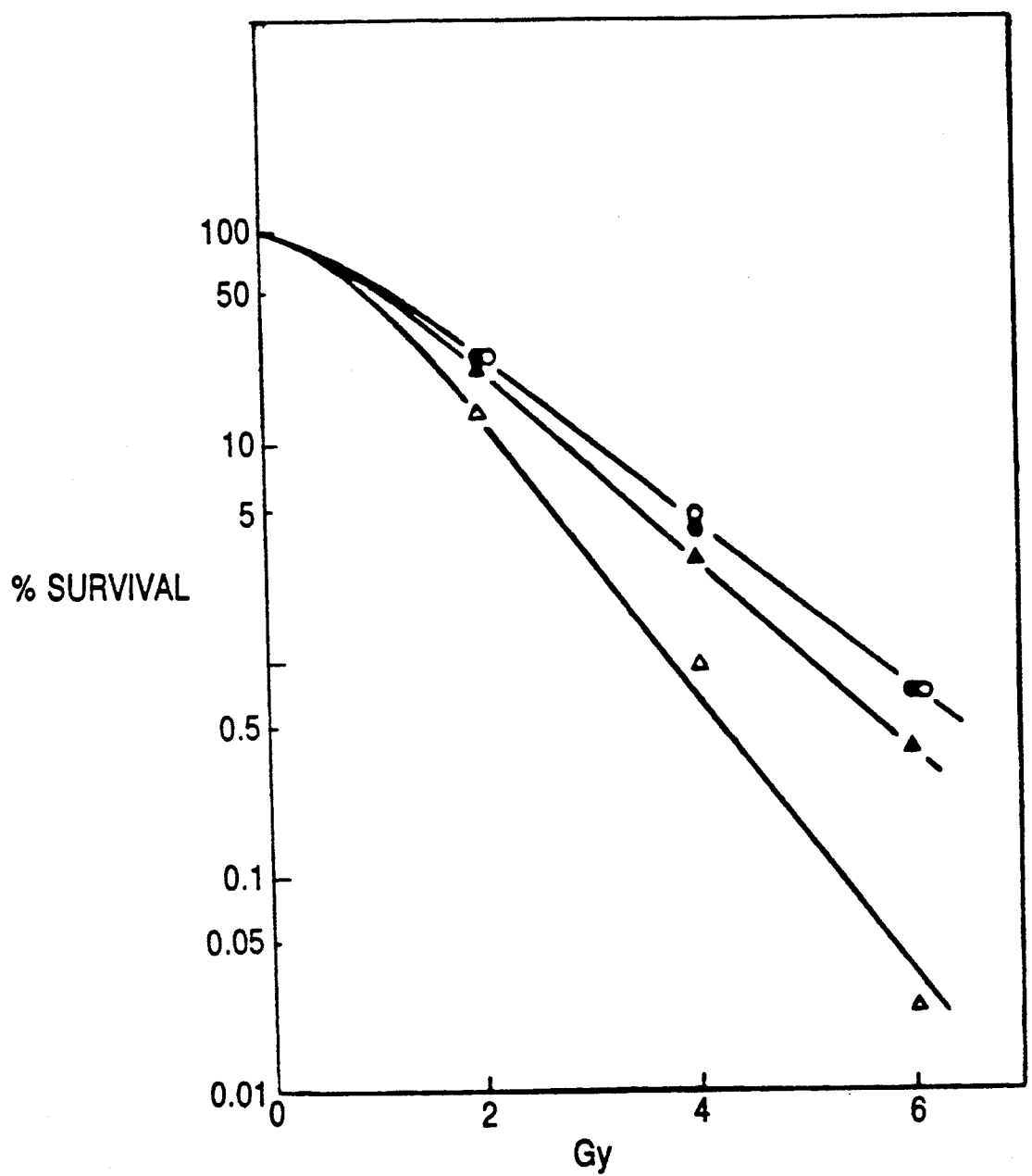
FIG. 13 shows cell survival curves of HeLa cells after a single dose of radiation alone (O), radiation plus heat (▲), radiation plus lonidamine (●), and combined radiation, heat and lonidamine (△). Lonidamine was present only during heating. Lonidamine had no cytotoxic effect on HeLa cells at 37° C.

The effect of trimodality therapy has been examined in HeLa monolayer cell cultures and in the transplanted Meth-A fibrosarcoma. The studies in HeLa cell cultures used a single radiation fraction, and prompt subculture for clonal analysis, conditions which would reduce any heat or drug-induced effect on potential lethal damage. As shown in FIG. 13, trimodality therapy of radiation therapy+lonidamine+mild hyperthermia (41.5° C.) was clearly superior to radiation alone, or bimodality therapy with either radiation+hyperthermia or radiation+lonidamine. In vivo comparative assessment of trimodality therapy versus single and bimodality combination was made in the oxic Meth-A fibrosarcoma. The trimodality regimen consisted of lonidamine (50 mg/kg/day chronically throughout the period of observation), plus radiation therapy (6 Gy×5), and hyperthermia (41.2° C.×65 min pre radiation therapy on days 1 and 4 of therapy); the results are presented in FIG. 14. Radiation therapy alone produced growth delay until day 11, and radiation therapy+lonidamine inhibition to day 13; radiation therapy+hyperthermia produced tumor regression, with regrowth commencing on day 18; trimodality therapy produced tumor regression to the point of non-palpability with regrowth not yet evident at day 32.

In Vivo Therapy Utilizing Lonidamine, Radiation and Hyperthermia

Localized radiation and hyperthermia was performed on BALB/cBy mice when tumors were 0.7+/−0.1 cucm and tumor analysis endpoints have been previously described. (26) Tumor control was defined as non-palpable tumor at 60 days. Waterbath temperatures were 41.7° C./65 minutes and 41.2° C./65 minutes×2 fractions. This resulted in tumor temperature equilibration at 5–7 minutes to 0.2°–0.3° C. (Bailey, 26 g thermocouple) below circulated water bath temperatures. Separation between the two hyperthermia treatments was 72 hours.

Lonidamine administration at hour pre-radiation and immediately hyperthermia and was based on serum pharmacokinetic and radiation studies (25). Animals were primed at 100 mg/kg. s.c., 3 days pre-radiation or hyperthermia. At the initiation of radiation or hyperthermia, animals were inoculated 50 mg/kg i.p. 1 hour before treatment and 50 mg/kg s.c. at 48 hours post treatment. Animals were maintained (100 mg/kg) during fractionation and post treatment until recurrence to initial volumes.

Results

Figure 14:
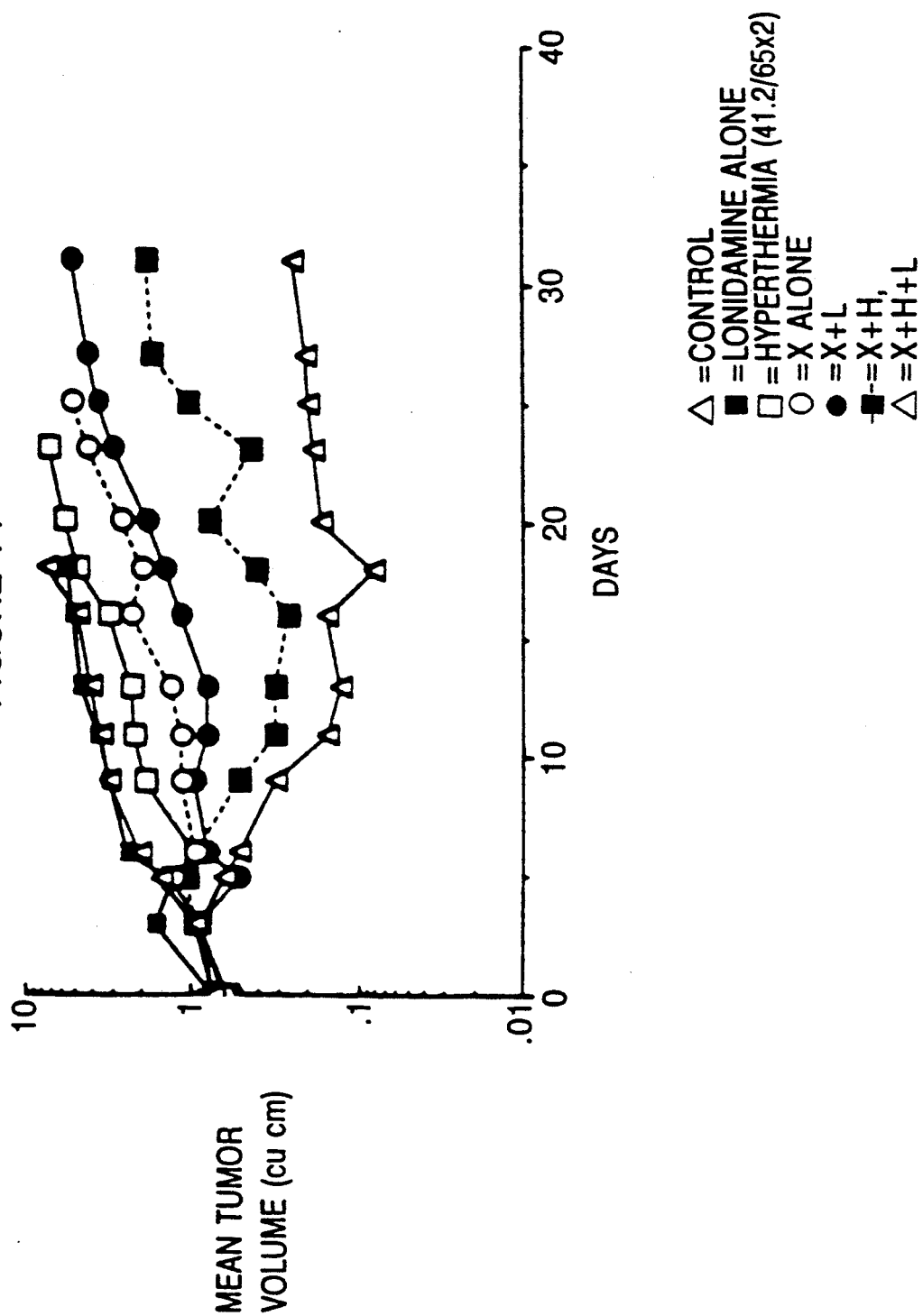
FIG. 14 shows vivo comparative assessment of trimodality therapy versus single and bimodality combination in the oxic Meth-A fibrosarcoma using lonidamine at 41.2° C.
Figure 16:
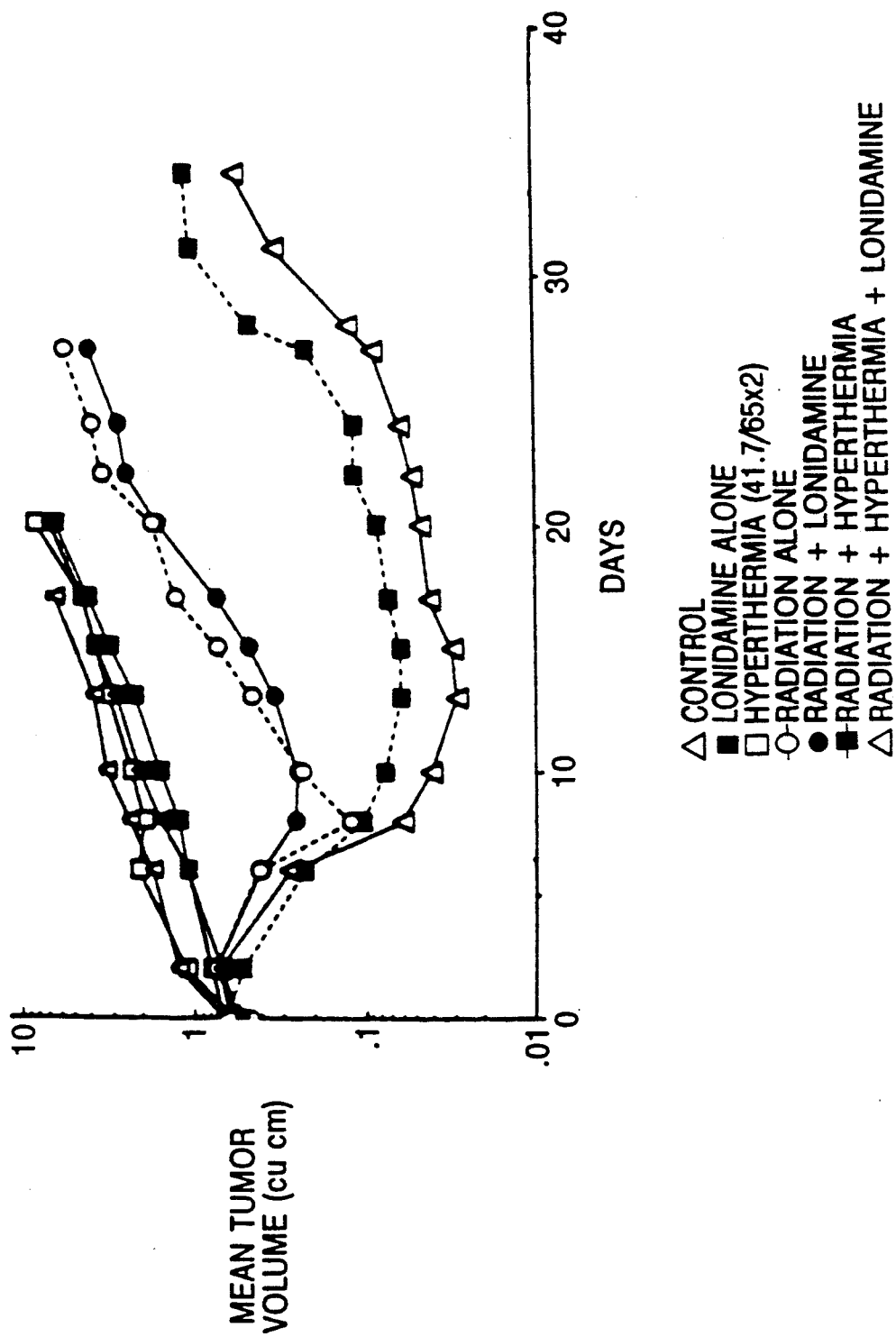
FIG. 16 shows the effect of fractionated radiation or hyperthermia at 41.7° C. and lonidamine.

The effect of fractionated radiation or hyperthermia at 41.2° C. or 41.7° C. and lonidamine are summarized in FIGS. 14 and 16. No differences were observed for the inter-group comparisons of lonidamine+hyperthermic versus hyperthermia alone or radiation+lonidamine versus radiation alone. Marginal differences in tumor response were seen when lonidamine was used in adjuvant capacity. Radiation at 41.7° C. was more effective than at 41.2° C., (50% and 16.7% tumor control respectively) and significantly greater than control observed with radiation alone. Tri-modality therapy (radiation+hyperthermia+lonidamine) provided comparable tumor control (50–56%) independent of temperature used and was more effective than the tumor control for radiation+hyperthermia at 41.2° C.

Temperatures were intended for vasodilation and increased tumor drug perfusion, to simulate tumor underheating and enhance sensitization by metabolic stress. The Hyperthermic sequence pre-radiation and after i.p. Lonidamine was considered optimal under the present format. Based on these rationale tri-modality therapy had a consistently greater effect when compared to single or bi-modality treatments.

The tumor response to fractionated 41° or 41.5° C. and radiation compared to radiation alone was not anticipated as this tumor has no significant hypoxic fraction associated with it (26). There is, however, tumor size dependent increased acidity as measured by 31P MR spectroscopy. (78) The pH reduction with growth could potentiate the lonidamine and/or hyperthermic interaction and this would correlate with the vitro cytotoxicity previously observed. (25, 26)

Clinical Studies with Lonidamine

Lonidamine has received extensive clinical assessment both as a single agent and in combination with radiation therapy. The dose-limiting side effect is skeletal muscle discomfort (37,38); however, at the commonly used clinical dosage of 150 mg t.i.d. it is well tolerated by most patients. In this dosage peak plasma levels of 5 to 15 μg/ml are attained; this is within the range that enhances the effect of radiation and hyperthermia in model systems (24-26, 30, 37 and 38). Two combined lonidamine+radiation therapy studies have been conducted in patients with extensive hepatic or brain metastases, respectively. Both of these trials were conducted prior to the availability of the cell culture data suggesting an advantage of chronic low dosage lonidamine; therefore, a single large daily dosage of lonidamine just prior to that day's radiation treatment was used. The Phase I study in patients with hepatic metastases showed acceptable patient tolerance of the combination; five of fifteen patients demonstrated objective tumor regression to radiation therapy dosages that ranged from 250 to 500 cGy ×5. The study in patients with brain metastases employed a randomized comparative design. Fifty eight patients were enrolled; 31 received lonidamine plus whole brain radiation therapy (WBRT) 300 cGy×10; 27 received WBRT alone. There was no significant difference in response or survival between the treatment groups (41). Peak plasma levels ≧15μg/ml were observed in 11 of 17 patients in the hepatic radiation therapy study and 15 of 30 patients in the WBRT study.

Figure 15:
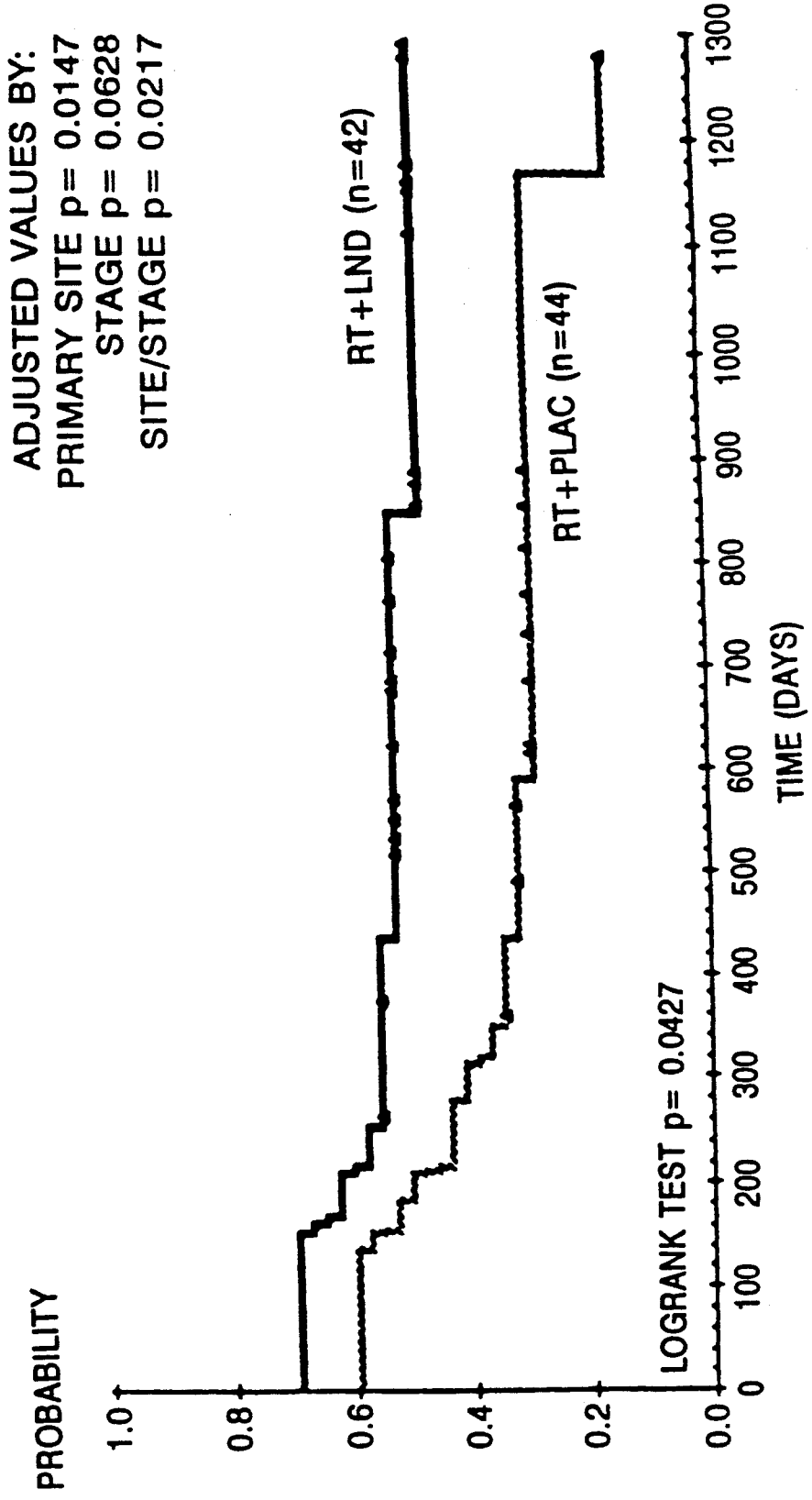
FIG. 15 illustrates the initial results of a placebo-controlled blinded trial of radiation therapy and lonidamine versus radiation therapy and placebo in 95 patients with stage 2-4 head and neck cancer.

Magno et al. (32) have reported the initial results of a placebo-controlled blinded trial of radiation therapy+lonidamine versus radiation therapy+placebo in 95 patients with Stage 2-4 head and neck cancer; the radiation therapy dosage was 60-66 Gy; the lonidamine dosage was 150 mg t.i.d. beginning 3 days prior to radiation therapy and containing for 3 months. The complete response rates were similar 69% (Radiation Therapy+Lonidamine) versus 58% (Radiation Therapy+Placebo), however, the remission duration was longer in the lonidamine treated arm. Disease free survival at 2 years (all patients) was 51% for Radiation Therapy+Lonidamine and 25% for Radiation Therapy+Placebo. The disease free survival curve from Magno's study is provided in FIG. 15.

Differences

1. Coleman, C. N. Hypoxia in tumors: A paradigm for the approach to biochemical and physiologic heterogeneity. J. Natl. Cancer Inst. 80:310-317 (1988).

2. Moulder, J. E. and Rockwell, S. Tumor hypoxia: Its impact on cancer therapy. Cancer and Metastasis Rev. 5:313-341 (1987).

3. Gatenby, R. A., Kessler, H. B., Rosenblum, J. S. Coia, L. R., Modolfsky, P. J., Hartz, W. H., and Broder, D. J. Oxygen distribution in squamous cell carcinoma metastases and its relationship to outcome of radiation therapy. Int. J. Radiation Oncol. Biol. Phys. 14:831-838 (1988).

4. Jain, R. K. Determinants of tumor blood flow: A review. Cancer Res. 48:2641-2658, (1988).

5. Chaplin, D. J., Durand, R. E., and Olive, P. E. Acute hypoxia in tumors: Implications for modifiers of radiation effects. Int. J. Radiation Oncology Biol. Phys. 12:1279-1282 (1986).

6. Chaplin, D. J. Olive, P. L., and Durand, R. E. Intermittent blood flow in a murine tumor: Radiobiological effects. Cancer Res. 47:597-601 (1987).

7. Van Den Berg, A. P., Wike-Hooley, J. L., Van Den BergBlok, A. E., Van Der Zee, J., and Reinhold, H. S. Tumor pH in human mammary carcinoma. Eur. J. Cancer Clin. Oncol. 18:457-462 (1982).

8. Thistlethwaite, A. J., Leeper, D. B., Moylan, D. J. III, and Nerlinger, R. E. pH distribution in human tumors. Int. J. Radiat. Oncol. Biol. Phys. 11:1647-1652 (1985).

9. Kim, J. H. Combined hyperthermia and radiation therapy in cancer treatment: Current status. Cancer Invest. 2:69-80 (1984).

10. Gerweck, L. E. Hyperthermia in cancer therapy: The biological basis and unresolved questions. Cancer Res. 45:3408-3414 (1985).

11. Kim, S. H., Kim, J. H., Hahn, E. W., and Ensign, N. A. Selective killing of glucose and oxygen-deprived HeLa cells by hyperthermia. Cancer Res. 40:3459-3462 (1980).

12. Nielsen, O. S. and Overgaard, J. Effect of extracellular pH on thermotolerance and recovery of hyperthermic damage in vitro. Cancer Res. 39:2772-2778 (1979).

13. Gerweck, L. E., Jennings, M., and Richards, B. Influence of pH on the response of cells to single and split doses of hyperthermia. Cancer Res. 40:4019-4024 (1980).

14. Kim, J. H., Hahn, E. W., and Ahmed, S. A. Combination hyperthermia and radiation therapy for malignant melanoma. Cancer 50:478-482 (1982).

15. Hiraoka, M., Jo, S., Dodo, Y. Ono, K., Takahashi, M., Nishida, H., and Abe, M. Clinical results of radiofrequency hyperthermia combined with radiation in the treatment of radioresistant cancers. Cancer 54:2898-2904 (1984).

16. Abe, M. Hiraoka, M., Takahashi, M., Egawa, S., Matsuda, C., Onoyama, Y., Morita, K., Hakehi, M., and Sugahara,. T. Multi-institutional studies on hyperthermia using an 8-MHz radiofrequency capacitive heating device (Thermotron RF-8) in combination with radiation for cancer therapy. Cancer 58:1589-1595 (1986).

17. Lindholm, C-E., Kjellen, E., Nilsson, P., and Hertzman, S. Microwave-induced hyperthermia and radiotherapy in human superficial tumors: Clinical results of a comparative study of combined treatment versus radiotherapy alone. Int. J. Hyperthermia 5:393-411 (1987).

18. Arcangeli, G. Benassi, M., Cividalli, A., Lovisolo, G. A., and Mauro, F. Radiotherapy and hyperthermia: Analysis of clinical results and identification of prognostic variables. Cancer 60:950-956 (1987).

19. Jonsson, G. G., Kjellen, E., Pero, R. W., Cameron, R. Radiosensitization effects of nicotinamide on malignant and normal mouse tissue. Cancer Res. 45:3609-3614 (1985).

20. Horsman, M. R., Brown, D. M., Lemmon, M. J., Brown, J. M., and Lee, W. W. Preferential tumor radiosensitization by analogs of nicotinamide and benzamide. Int. J. Radiat. Oncol. Biol. Phys. 12:1307-1310 (1986).

21. Horsman, M. R., Chaplin, D. J., and Brown, D. M. Radiosensitization by nicotinamide in vivo: A greater enhancement of tumor damage compared to that of normal tissues. Radiation Res. 109:479-489 (1987).

22. Kim, J. H., Alfieri, A. A., and Kim, S. H. Radiosensitization of a hypoxic murine mammary adenocarcinoma by combined nicotinamide and hyperthermia, Cancer Res. In Press.

23. Hoffer, A. Safety, side effects and relative lack of toxicity of nicotinic acid and nicotinamide. Schizophrenia 1:78-87 (1969).

24. Kim, J. H., Kim, S. H. Alfieri, A., and Young, C. W., and Silverstrini, B. Lonidamine: A hyperthermic sensitizer of HeLa cells in culture and of the Meth-A tumor in vivo. Oncology (Basel), 41 (Suppl. 1):30-35 1984.

25. Kim, J. H., Alfieri, A. A., Kim, S. H., and Young, C. W., Radiosensitization of Meth-A fibrosarcoma in mice by lonidamine. Oncology (Basel), 41 (Suppl. 1):36–38 (1984).

26. Kim, J. H., Alfieri, A. A., Kim, S. H., and Young, C. W., Potentiation of radiation effects on two murine tumors by lonidamine. Cancer Res. 46:1120–1123 (1986).

27. Floridi, A., Paggi, M. G., Marcante, M. L., Silverstrini, B., Caputo, A., and DeMartino, C., Lonidamine, a selective inhibitor of aerobic glycolysis of murine tumor cells, J. Natl. Cancer Inst. 66:497–499 (1981).

8. Floridi, A., Paggi, M. G. D'Atri, S., DeMartino, C., Marcante; M. L., Silvestrini, B., and Caputo, A., Effect of lonidamine on the energy metabolism of Ehrlich ascites tumor cells. Cancer Res. 41:4661–4666 (1981).

29. Hahn, G. M., Van Kersen, I., Silvestrini, B. Inhibition of the recovery from potentially lethal damage by lonidamine. Br. J. Cancer 50:657–660 (1984).

30. Kim, J. H., Kim, S. H., He, S. Q., Alfieri, A. A., and Young, C. W. Potentiation of radiation effects on multicellular tumor spheroids of HeLa cells by lonidamine. Int. J. Rad. Oncol. In Press.

31. Kim, S. H., Kim, J. H., Alfieri, A. A., He, S. Q., and Young, C. W., Gossypol, a hyperthermic sensitizer of HeLa cells. Cancer Res. 45:6338–6340, 1985.

32. Magno, L., Terraneo, F., Scandolaro, L. Bertoni, F., DeGregorio, M., and Ciottoli, G. B., Lonidamine and radiotherapy in head and neck cancer: A preliminary report. Proc. Amer. Soc. Clin. Oncol. 6:126 (1987).

33. Herman, T. S., Teicher, B. A., Jochelson, M., Clark, J., Svensson, G., and Coleman, C. N., Rationale for use of local hyperthermia with radiation therapy and selected anticancer drugs in locally advanced human malignancies. Int. J. Hyperthermia 4:143–158 (1988).

34. Kim, J. H., Kim, S. H., and Alfieri, A. Unpublished observations.

35. Hiraoka, M., Jo, S., Akuta, K., Nishimura, Y., Takahashi, M., and Abe, M., Radiofrequency capacitive hyperthermia for deep-seated tumors. I. Studies on thermometry. Cancer 60:121–127 (1987).

36. Hirako, M., Jo, S., Akuto, K., Nishimura, Y., Takahashi, M., and Abe, M., Radiofrequency capacitive hyperthermia for deep seated tumors. II. Effects of thermoradiotherapy. Cancer 60:128–135 (1987).

37. Young, C. W., Currie, V. E., Kim, J. H., O'Hehir, M. A., Farag, F. M., and Kinahan, J. E., Phase I and clinical pharmacologic evaluation of lonidamine in patients with advanced cancer. Oncology (Basel), 41 (Suppl. 1):60–65 (1984).

38. Besner, J. G., Leclair, R., Band, P. R., Deschamps, M., DeSanctis, A. J., and Catanese, B., Pharmacokinetics of lonidamine, after oral administration in cancer patients. Oncology (Basel), 41 (Suppl. 1):48–52 (1984).

39. Leclaire, R., Besner, J. G., Band, P., Mailhot, S., Gervais, P., DeSanctis, A., and Deschamps, M., High performance liquid chromatography of lonidamine in human plasma and urine. J. Chromatog. 277 427–432 (1983).

40. Currie, V. E., Kim, J. H., and Young, C. W., Unpublished observations.

41. DeAngelis, L. M. Curie, V. E., Kim, J. H., Krol, G., O'Hehir, M., Garag. F. M., Young, C. W., and Posner, J. B., The combined use of radiation therapy and lonidamine in the treatment of brain metastases. J. Neuro-Oncology, In Press.

42. Kaelin, W. G., Jr., Shrivastav, S., and Jirtle, R. L., Blood flow to primary tumors and lymph node metastases in SMT-2A tumor-bearing rats following intravenour flurnarizine. Cancer Res. 44:896–899 (1984).

43. Shibata, K., Kawada, T., and Iwai, K., High-performance liquid chromatographic determination of nicotinamide in rat tissue samples and blood after extraction with diethyl ether. J. Chromatog. 422:257–262 (1987).

44. Kinsella, T. J. and Glatstein, E., Clinical experience with intravenous radiosensitizers in unresectable sarcomas. Cancer 59:908–915 (1987).

45. Valdagni, R., Amichetti, M., and Pani, G., Radical radiation alone versus radical radiation plus microwave hyperthermia for $N_3$ (TNM-UICC) neck nodes: A prospective randomized clinical trial. Int. J. Radiation Oncology Biol. Phys. 15:13–24 (1988).

46. Valdagni, R., Liu, F-F., and Kapp, D. S., Important prognostic factors influencing outcome of combined radiation and hyperthermia. Int. J. Radiation Oncology Biol. Phys. 15:959–972 (1988).

47. Dragovic, J., Seydel, H. G., Sandhu, T., Kolosvary, A., and Blough, J., Local superficial hyperthermia in combination with low-dose radiation therapy for palliation of locally recurrent breast carcinoma. J. Clin. Oncol. 7:30–35 (1989).

48. Gonzalez, D., Van Dijk, J. D. P., Blank, L. E. C., and Rumke, Ph., combined treatment with radiation and hyperthermia in metastatic malignant melanoma. Radiother. and Oncol. 6:105–113 (1986).

49. Kim, J. H., Hahn, E. W., Ahmed, S. A., and Kim, J. S.: Clinical study of the sequence of combined hyperthermia and radiation therapy of malignant melanoma. In Hyperthermic Oncology, 1984, Vol. J. Overgaard (Ed.). London, Philadelphia, Taylor and Francis. 1984, pp. 387–390.

50. Overgaard, J., Overgaard, M., Vejby Hansen, P., and von der Maase, H., Some factors of importance in the radiation treatment of malignant melanoma. Radiotherapy and Oncology 5:183–192 (1986).

51. Emami, B., Perez, C. A. Konefal, J., Pilepich, M. V., Leybovich, L., Straube, W., VonGerichten, D., and Hederman, M. A. Thermoradiotherapy of malignant melanoma, Int. J. Hyperthermia 4:373–381 (1988).

52. Overgaard, J. and Overgaard, M., Hyperthermia as an adjuvant to radiotherapy in the treatment of malignant melanoma. Int. J. Hyperthermia 3:483–501 (1987).

53. Perez, C. A. and Meyer, J. L., Clinical experience with localized hyperthermia and irradiation. In Hyperthermic Oncology 1984, pp. 181–198.

54. Gatenby, R. A., Coia, L. R., Richter, M. P., Katz, H., Moldofsky, P. J., Engstrom, P., Brown, D. Q., Brookland, R., and Broder, G. J. Oxygen tension in human tumors: In vivo mapping using CT-guided probes. Radiology 156:211–214 (1985).

55. Jackson, Progress Towards a Male Contraceptive II: vol. 8, pp. 145–157 (New York: John Wiley and Sons, Ltd.) (1982).

56. Kalla, IRCS-Med. Sci. 10:766–769 (1982).

57. Sang, Hormones In Normal and Abnormal Tissues III, pp. 215–249 (Berlin - New York: Walter de Gruyler and Co.) (1983).

58. Haspel et al. J. Pharmacol, Exp. Ther. 299: 218-225 (1984).
59. Tuszynski et al., Cancer Res. 44:768-771 (1984).
60. Wong et. al., Cancer Res. 44: 35-38 (1984).
61. Ye et al., In Vitro 19:5314 57 (1983).
62. Abou-Donia et al., Life Sci. 14:1955-1963 (1984).
63. Abou-Donia, Residue Rev. 61: 125-160 (1976).
64 Adeyemo et al., Arch. Androl 9:343-349 (1982).
65. Bi et al., Scientia Sinica 24:573-580 (1981).
66. Corin et al., J. Biol. Chem. 259:206-211 (1984).
67. Haspel et al., Fed. Proc. 41:671 (1982).
68. Hong et al., Toxicol. Appl. Pharmacal. 71:430-435 (1983).
69. Reyes et al., J. Biol. Chem. 259:9607-9615 (1984).
70. Tso et al., Contraception 24:569-576 (1981).
71. Tso et al. Arch. Andol. 9:31-32 (1982).
72. Chen et al., Cold Spring Harbor Symp. Quant. Biol. 46:141-155 (1982).
73. Darzynkiewicz et al., Cancer Res 42:799-806 (1982).
74. Bernal et al., lnt. J. Canc. 30:219-224 (1982).
75. Lampides et al., Cancer Res. :43:716-720 (1983).
76. Kim et al., Science 200:206-207 (1978) (5-thio-D-glycose; hypoxic tumor cells).
77. Kim et al., Cancer Res. 38:2935-2938 (1978) (5-thio-D-glycose; hypoxic tumor cells).
78. Koutcher et al. Abst. International Journal of Radiation Oncology, Biology and physics, 12:256 (1987).

What is claimed is:

1. A method of treating a patient with brain or hepatic metastases which comprises first administering to the patient an amount of lonidamine effective to enhance the sensitivity of such metastases to a subsequent application of heat and radiation, then applying heat and radiation to the metastases, such heat being applied in an amount sufficient to raise the temperature of the metastases above 41° C. and such radiation being applied in an amount of 15 Gy to 65 Gy, so as to inhibit proliferation of the metastases, and thereby treating the patient with brain or hepatic metastases.

2. The method of claim 1, wherein the heat and radiation are applied concurrently.

3. The method of claim 8, wherein the application of radiation is subsequent to the application of heat.

4. The method of claims 1, wherein the radiation applied to the tumor is election radiation or photon radiation.

5. The method of claim 1, wherein the effective amount of heat applied to the tumor cells is an amount which is sufficient to raise the temperature of the tumor to above about 38° C.

6. The method of claim 1, wherein the effective amount of heat applied to the tumor cells is an amount which is sufficient to raise the temperature of the tumor to above about 41° C.

7. The method of claim 1, wherein the sensitizing compound is administered orally to the patient.

8. The method of claim 1, wherein the effective amount is from about 25 mg/kg/day to about 200 mg/kg/day.

9. The method of claim 1, wherein the lonidamine is administered intraperenterally.

10. The method of claim 1 wherein the metastases are deep-seated metastases.

* * * * *